(12) United States Patent
De Juan, Jr. et al.

(10) Patent No.: US 8,591,025 B1
(45) Date of Patent: Nov. 26, 2013

(54) EYE COVERING AND REFRACTIVE CORRECTION METHODS FOR LASIK AND OTHER APPLICATIONS

(71) Applicant: NexisVision, Inc., Menlo Park, CA (US)

(72) Inventors: Eugene De Juan, Jr., San Francisco, CA (US); Cary J. Reich, Los Gatos, CA (US); Yair Alster, Palo Alto, CA (US); Matt Clarke, Menlo Park, CA (US); Kuangmon Ashley Tuan, Mountain View, CA (US); Brian Levy, New York, NY (US)

(73) Assignee: NexisVision, Inc., Menlo Park, CA (US)

( * ) Notice: Subject to any disclaimer, the term of this patent is extended or adjusted under 35 U.S.C. 154(b) by 0 days.

(21) Appl. No.: 13/715,917

(22) Filed: Dec. 14, 2012

Related U.S. Application Data

(60) Provisional application No. 61/699,747, filed on Sep. 11, 2012.

(51) Int. Cl.
G02C 7/04 (2006.01)

(52) U.S. Cl.
USPC ......... 351/159.04; 606/5; 623/5.11; 623/5.13

(58) Field of Classification Search
USPC ................. 606/5; 351/159.04; 623/5.11–5.14
See application file for complete search history.

(56) References Cited

U.S. PATENT DOCUMENTS

| | | | |
|---|---|---|---|
| 2,641,161 A | 6/1953 | Silverstein | |
| 3,246,941 A | 4/1966 | Moss | |
| 3,488,111 A | 1/1970 | Isen | |
| 3,489,491 A | 1/1970 | Creighton | |
| 3,495,899 A | 2/1970 | Biri | |
| 3,619,044 A | 11/1971 | Kamath | |
| 3,688,386 A | 9/1972 | Pereira | |
| 3,833,786 A | 9/1974 | Brucker | |
| 3,915,609 A | 10/1975 | Robinson | |
| 3,944,347 A | 3/1976 | Barkdoll et al. | |
| 3,973,837 A | 8/1976 | Page | |
| 3,973,838 A | 8/1976 | Page | |

(Continued)

FOREIGN PATENT DOCUMENTS

| | | |
|---|---|---|
| CA | 2174967 C | 5/1995 |
| DE | 3143839 A1 | 5/1983 |

(Continued)

OTHER PUBLICATIONS

International Search Report and Written Opinion of the International Searching Authority for PCT Application No. PCT/US2010/053975, mailed Feb. 11, 2011, 30 pages.

(Continued)

*Primary Examiner* — Bill Thomson
*Assistant Examiner* — Jeffrey Lipitz
(74) *Attorney, Agent, or Firm* — Kilpatrick Townsend & Stockton LLP

(57) ABSTRACT

A method for providing faster visual and functional recovery of patients following refractive surgery such as laser assisted in situ keratomileusis (LASIK) is disclosed. The method comprises providing a covering to the eye of a patient comprising an inner portion having an inner rigidity and at least one inner radius of curvature; and an outer portion having an outer rigidity and at least one outer radius of curvature; wherein the inner rigidity is greater than the outer rigidity.

18 Claims, 25 Drawing Sheets

(56) References Cited

U.S. PATENT DOCUMENTS

| | | |
|---|---|---|
| 4,037,866 A | 7/1977 | Price |
| 4,053,442 A | 10/1977 | Jungr et al. |
| 4,068,933 A | 1/1978 | Seiderman |
| 4,071,272 A | 1/1978 | Drilik |
| 4,121,885 A | 10/1978 | Erickson et al. |
| 4,166,255 A | 8/1979 | Graham |
| 4,171,878 A | 10/1979 | Kivaev et al. |
| 4,194,815 A | 3/1980 | Trombley |
| 4,200,320 A | 4/1980 | Durham |
| 4,208,362 A | 6/1980 | Ceichert et al. |
| 4,211,476 A | 7/1980 | Brummel et al. |
| 4,312,575 A | 1/1982 | Peyman et al. |
| 4,487,905 A | 12/1984 | Mitchell |
| 4,621,912 A | 11/1986 | Meyer |
| 4,666,249 A | 5/1987 | Bauman et al. |
| 4,666,267 A | 5/1987 | Wickterle |
| 4,701,288 A | 10/1987 | Cook et al. |
| 4,772,283 A | 9/1988 | White |
| 4,806,382 A | 2/1989 | Goldberg et al. |
| 4,810,082 A | 3/1989 | Abel, Jr. |
| 4,886,350 A | 12/1989 | Wichterle |
| 4,890,911 A | 1/1990 | Sulc et al. |
| 4,909,896 A | 3/1990 | Ikushima et al. |
| 4,940,751 A | 7/1990 | Frances et al. |
| 4,943,150 A | 7/1990 | Diechert et al. |
| 4,952,045 A | 8/1990 | Stoyan |
| 4,978,481 A | 12/1990 | Janssen et al. |
| 4,997,583 A | 3/1991 | Itzhak |
| 5,008,289 A | 4/1991 | Bernstein |
| 5,104,213 A | 4/1992 | Wolfson |
| 5,143,660 A | 9/1992 | Hamilton et al. |
| 5,178,879 A | 1/1993 | Adekunle et al. |
| 5,191,365 A | 3/1993 | Stoyan |
| 5,236,236 A | 8/1993 | Girimont |
| 5,245,367 A | 9/1993 | Miller et al. |
| 5,246,259 A | 9/1993 | Hellenkamp et al. |
| 5,293,186 A | 3/1994 | Seden et al. |
| 5,347,326 A | 9/1994 | Volk |
| 5,349,395 A | 9/1994 | Stoyan |
| 5,397,848 A | 3/1995 | Yang et al. |
| 5,428,412 A | 6/1995 | Stoyan |
| 5,433,714 A | 7/1995 | Bloomberg |
| 5,433,898 A | 7/1995 | Thakrar et al. |
| 5,472,436 A | 12/1995 | Fremstad |
| 5,496,084 A | 3/1996 | Miralles Medan |
| 5,517,260 A | 5/1996 | Glady et al. |
| 5,538,301 A | 7/1996 | Yavitz et al. |
| 5,570,144 A | 10/1996 | Lofgren-Nisser |
| 5,578,332 A | 11/1996 | Hamilton et al. |
| 5,598,233 A | 1/1997 | Haralambopoulos et al. |
| 5,662,706 A | 9/1997 | Legerton et al. |
| 5,671,038 A | 9/1997 | Porat |
| 5,732,990 A | 3/1998 | Yavitz et al. |
| 5,757,458 A | 5/1998 | Miller et al. |
| 5,760,100 A | 6/1998 | Nicolson et al. |
| 5,760,870 A | 6/1998 | Payor et al. |
| 5,854,291 A | 12/1998 | Laughlin et al. |
| 5,869,533 A | 2/1999 | Holt |
| 5,885,597 A | 3/1999 | Botknecht et al. |
| 5,905,561 A | 5/1999 | Lee et al. |
| 5,910,512 A | 6/1999 | Conant |
| 5,923,397 A | 7/1999 | Bonafini, Jr. |
| 5,929,968 A | 7/1999 | Cotie et al. |
| 5,953,098 A | 9/1999 | Lieberman et al. |
| 5,962,532 A | 10/1999 | Campbell et al. |
| 5,980,040 A | 11/1999 | Xu et al. |
| 5,986,001 A | 11/1999 | Ingenito et al. |
| 6,010,219 A | 1/2000 | Stoyan |
| 6,030,974 A | 2/2000 | Schwartz et al. |
| 6,036,314 A | 3/2000 | Wolfson |
| 6,048,855 A | 4/2000 | De Lacharriere et al. |
| 6,075,066 A | 6/2000 | Matsuda et al. |
| 6,099,121 A | 8/2000 | Chapman et al. |
| 6,217,171 B1 | 4/2001 | Auten et al. |
| 6,244,709 B1 | 6/2001 | Vayntraub et al. |
| 6,248,788 B1 | 6/2001 | Robbins et al. |
| 6,325,509 B1 | 12/2001 | Hodur et al. |
| 6,340,229 B1 | 1/2002 | Lieberman et al. |
| 6,361,169 B1 | 3/2002 | Tung |
| 6,364,482 B1 | 4/2002 | Roffman et al. |
| 6,406,145 B1 | 6/2002 | Jubin |
| 6,520,637 B2 | 2/2003 | Hodur et al. |
| 6,541,028 B1 | 4/2003 | Kuri-Harcuch et al. |
| 6,551,307 B2 | 4/2003 | Peyman |
| 6,579,918 B1 | 6/2003 | Auten et al. |
| 6,593,370 B2 | 7/2003 | Tamura et al. |
| 6,652,095 B2 | 11/2003 | Tung |
| 6,659,607 B2 | 12/2003 | Miyamura et al. |
| 6,726,322 B2 | 4/2004 | Andino et al. |
| 6,843,563 B2 | 1/2005 | Richardson |
| 6,849,671 B2 | 2/2005 | Steffen et al. |
| 6,951,894 B1 | 10/2005 | Nicolson et al. |
| 7,018,039 B2 | 3/2006 | Legerton et al. |
| 7,025,455 B2 | 4/2006 | Roffman |
| 7,080,905 B2 | 7/2006 | Marmo et al. |
| 7,097,301 B2 | 8/2006 | Legerton et al. |
| 7,104,648 B2 | 9/2006 | Dahi et al. |
| 7,150,529 B2 | 12/2006 | Legerton et al. |
| 7,163,292 B2 | 1/2007 | Dahi et al. |
| 7,193,124 B2 | 3/2007 | Coffee |
| 7,216,974 B2 | 5/2007 | Meyers et al. |
| 7,249,849 B2 | 7/2007 | Marmo et al. |
| 7,270,412 B2 | 9/2007 | Legerton et al. |
| 7,322,694 B2 | 1/2008 | Dahi et al. |
| 7,329,001 B2 | 2/2008 | Benrashid et al. |
| 7,338,160 B2 | 3/2008 | Lieberman et al. |
| 7,360,890 B2 | 4/2008 | Back |
| 7,377,637 B2 | 5/2008 | Legerton et al. |
| 7,401,922 B2 | 7/2008 | Legerton |
| 7,404,638 B2 | 7/2008 | Miller et al. |
| 7,461,937 B2 | 12/2008 | Steffen et al. |
| 7,491,350 B2 | 2/2009 | Silvestrini |
| 7,530,689 B2 | 5/2009 | Berke |
| 7,537,339 B2 | 5/2009 | Legerton et al. |
| 7,543,936 B2 | 6/2009 | Legerton et al. |
| 7,559,649 B2 | 7/2009 | Cotie et al. |
| 7,585,074 B2 | 9/2009 | Dahi et al. |
| 7,594,725 B2 | 9/2009 | Legerton et al. |
| 7,628,810 B2 | 12/2009 | Christie et al. |
| 7,682,020 B2 | 3/2010 | Berke |
| 7,695,135 B1 | 4/2010 | Rosenthal |
| 7,699,465 B2 | 4/2010 | Dootjes et al. |
| 7,717,555 B2 | 5/2010 | Legerton et al. |
| 7,735,997 B2 | 6/2010 | Muckenhirn |
| 7,748,844 B2 | 7/2010 | Lai |
| 7,828,432 B2 | 11/2010 | Meyers et al. |
| 7,859,769 B2 | 12/2010 | Zalevsky |
| 7,976,577 B2 | 7/2011 | Silvestrini |
| 7,984,988 B2 | 7/2011 | Berke |
| 8,201,941 B2 | 6/2012 | Choo et al. |
| 2002/0095199 A1 | 7/2002 | West, Jr. et al. |
| 2004/0088050 A1 | 5/2004 | Norrby et al. |
| 2004/0141150 A1 | 7/2004 | Roffman et al. |
| 2004/0170666 A1 | 9/2004 | Keates et al. |
| 2004/0184158 A1 | 9/2004 | Shadduck |
| 2005/0033420 A1 | 2/2005 | Christie et al. |
| 2005/0107775 A1 | 5/2005 | Huang et al. |
| 2005/0259221 A1 | 11/2005 | Marmo |
| 2005/0288196 A1 | 12/2005 | Horn |
| 2006/0077581 A1 | 4/2006 | Schwiegerling et al. |
| 2006/0083773 A1 | 4/2006 | Myung et al. |
| 2006/0132707 A1 | 6/2006 | Tung |
| 2006/0152673 A1 | 7/2006 | Cotie et al. |
| 2006/0197909 A1 | 9/2006 | Legerton |
| 2006/0197910 A1 | 9/2006 | Legerton |
| 2006/0238712 A1 | 10/2006 | Dahi |
| 2006/0241751 A1 | 10/2006 | Marmo |
| 2006/0250576 A1* | 11/2006 | Legerton et al. .............. 351/177 |
| 2006/0256283 A1 | 11/2006 | Legerton |
| 2006/0256284 A1 | 11/2006 | Dahi |
| 2006/0285072 A1 | 12/2006 | Dahi |
| 2006/0290882 A1 | 12/2006 | Meyers et al. |
| 2007/0013869 A1 | 1/2007 | Dahi |
| 2007/0014760 A1 | 1/2007 | Peyman |

(56) References Cited

U.S. PATENT DOCUMENTS

| | | |
|---|---|---|
| 2007/0037898 A1 | 2/2007 | Phelan et al. |
| 2007/0046894 A1 | 3/2007 | Muckenhirn |
| 2007/0106394 A1 | 5/2007 | Chen |
| 2007/0242216 A1 | 10/2007 | Dootjes et al. |
| 2007/0244559 A1 | 10/2007 | Shiuey |
| 2007/0273834 A1 | 11/2007 | Legerton |
| 2008/0039832 A1 | 2/2008 | Palanker et al. |
| 2008/0074611 A1* | 3/2008 | Meyers et al. ............ 351/160 R |
| 2008/0291391 A1 | 11/2008 | Meyers et al. |
| 2009/0237612 A1 | 9/2009 | Cotie et al. |
| 2009/0303442 A1 | 12/2009 | Choo et al. |
| 2010/0036488 A1 | 2/2010 | De Juan, Jr. et al. |
| 2010/0060849 A1 | 3/2010 | Hibino |
| 2010/0128224 A1 | 5/2010 | Legerton |
| 2010/0157250 A1 | 6/2010 | Berke |
| 2010/0208196 A1 | 8/2010 | Benrashid et al. |
| 2010/0271589 A1 | 10/2010 | Legerton et al. |
| 2011/0208300 A1 | 8/2011 | De Juan, Jr. et al. |
| 2012/0105804 A1 | 5/2012 | Legerton |
| 2012/0113386 A1 | 5/2012 | Back |
| 2012/0169994 A1 | 7/2012 | Matsushita et al. |
| 2012/0310133 A1 | 12/2012 | De Juan, Jr. et al. |

FOREIGN PATENT DOCUMENTS

| | | |
|---|---|---|
| EP | 42679 A2 | 12/1981 |
| EP | 0434205 A2 | 6/1991 |
| EP | 638416 A1 | 11/1995 |
| GB | 2107895 A | 5/1983 |
| WO | 90/14083 A1 | 11/1990 |
| WO | 95/13764 A1 | 5/1995 |
| WO | 96/27816 A1 | 9/1996 |
| WO | 97/19381 A1 | 5/1997 |
| WO | 98/03267 A1 | 1/1998 |
| WO | 99/30560 A1 | 6/1999 |
| WO | 99/43354 A2 | 9/1999 |
| WO | 99/43354 A3 | 9/1999 |
| WO | 99/46631 A1 | 9/1999 |
| WO | 00/09042 A1 | 2/2000 |
| WO | 01/68082 A1 | 9/2001 |
| WO | 02/068008 A1 | 9/2002 |
| WO | 03/097759 A1 | 11/2003 |
| WO | 2004/068196 A1 | 8/2004 |
| WO | 2004/097502 A1 | 11/2004 |
| WO | 2004/109368 A2 | 12/2004 |
| WO | 2005/079290 A2 | 9/2005 |
| WO | 2005/116729 A2 | 12/2005 |
| WO | 2006/026666 A2 | 3/2006 |
| WO | 2006/026666 A3 | 3/2006 |
| WO | 2006/121591 A1 | 11/2006 |
| WO | 2007/002231 A1 | 1/2007 |
| WO | 2007/044513 A1 | 4/2007 |
| WO | 2007/053297 A2 | 5/2007 |
| WO | 2007/053297 A3 | 5/2007 |
| WO | 2009/065061 A1 | 5/2009 |
| WO | 2006/113149 A2 | 10/2009 |
| WO | 2006/113149 A3 | 10/2009 |
| WO | 2009/145842 A2 | 12/2009 |
| WO | 2010/051172 A1 | 5/2010 |
| WO | 2011/050327 A1 | 4/2011 |
| WO | 2011/050365 A1 | 4/2011 |
| WO | 2012/061160 A1 | 5/2012 |
| WO | 2012/149056 A1 | 11/2012 |

OTHER PUBLICATIONS

International Preliminary Report on Patentability for PCT Application No. PCT/US2010/053975, dated Apr. 24, 2012, 20 pages.

International Search Report and Written Opinion of the International Searching Authority for PCT Application No. PCT/US2010/053854, mailed Mar. 1, 2011, 18 pages.

International Preliminary Report on Patentability for PCT Application No. PCT/US2010/053854, dated Apr. 24, 2012, 13 pages.

International Search Report and Written Opinion of the International Searching Authority for PCT Application No. PCT/US2009/002166, mailed Nov. 19, 2009, 13 pages.

International Preliminary Report on Patentability for PCT Application No. PCT/US2009/002166, dated Oct. 5, 2010, 5 pages.

International Search Report for PCT/US2011/57755, mailed on Feb. 7, 2012, 3 pages.

International Search Report and Written Opinion of the International Searching Authority for PCT Application No. PCT/US2012/035050, mailed Oct. 3, 2012, 12 pages.

Bissen-Miyajima et al., "Role of the endothelial pump in flap adhesion after laser in situ keratomileusis," J Cataract Refract Surg. Sep. 2004; 30(9): pp. 1989-1992.

Bausch & Lomb Boston® Materials & Solutions Product Guide, 2009, 38 pages total.

SynergEyes, Inc., SynergEyes® A Practitioner Training, retrieved from the Internet: <http://www.fitsynergeyes.com/syn_a/synergeyesA_presentation.pdf>, 52 pages.

SynergEyes, Inc., "SynergEyes® A," [package insert, P/N 70008 Rev. I], 12 pages.

SynergEyes®, Inc., Product Overview of CLEARKONE® and SYNERGEYES® PS retrieved from the Internet http://www.synergeyes.com/index.html on May 29, 2012, 5 pages.

* cited by examiner

EYE COVERING AND REFRACTIVE CORRECTION METHODS FOR LASIK AND OTHER APPLICATIONS

This application claims the benefit under 35 U.S.C. §119(e) of U.S. Provisional Application No. 61/699,747 filed on Sep. 11, 2012, which is incorporated by referenced in its entirety.

FIELD

The present disclosure is generally directed to vision and treatment of the eye to provide improved vision. The disclosed methods and devices may, for example, provide for faster visual and functional recovery of patients following refractive surgery such as laser-assisted in situ keratomileusis (LASIK). In some embodiments, the methods comprise providing a covering to the eye of a patient wherein the covering comprises an inner portion having an inner rigidity and at least one inner radius of curvature; and an outer portion having an outer rigidity and at least one outer radius of curvature; wherein the inner rigidity is greater than the outer rigidity.

BACKGROUND

The eye includes several tissues that allow patients to see. The cornea of the eye is an anterior tissue of the eye that is clear in healthy eyes and refracts light so as to form an image on the retina. The retina is a posterior tissue of the eye that senses light from the image formed thereon and transmits signals from the image to the brain. The cornea includes an outer layer of tissue, the epithelium, which protects the underlying tissues of the cornea, such as Bowman's membrane, the stroma and nerve fibers that extend into the stroma and Bowman's membrane. The healthy eye includes a tear film disposed over the epithelium. The tear film can smooth small irregularities of the epithelium so as to provide an optically smooth surface. The tear film is shaped substantially by the shape of the underlying epithelium, stroma, and Bowman's membrane, if present. The tear film comprises a liquid that is mostly water and does include additional components, such as mucoids and lipids. The many nerve fibers of the cornea provide sensation to promote blinking that can cover the cornea with the tear film. The nerve fibers also sense pain so that one will normally avoid trauma to the cornea and also avoid direct contact of an object to the cornea so as to protect this important tissue.

Refractive eye surgery is used to improve the refractive state of the eye and includes procedures such as, for example, automated lamellar keratoplasty (ALK), laser assisted in-situ keratomileusis (LASIK), photorefractive keratectomy (PRK), laser assisted sub-epithelium keratomeleusis (LASEK), EPI-LASIK, radial keratotomy, mini-asymmetric radial keratotomy, arcuate kertotomy, limbal relaxing incisions, thermal keratoplasty, laser thermal keratoplasty, intrastomal corneal ring segment removal, and phakic intraocular lens implantation. Following any of these procedures there is a period of time before optimal vision is restored. For example, in LASIK, optimal vision is typically achieved within about 24 hours following surgery. During this recovery period, in addition to sub-optimal visual acuity, a patient may experience discomforts such as photophobia or light sensitivity and/or a burning sensation. Methods for reducing the time to achieve optimal vision and for reducing or eliminating discomfort associated with refractive eye surgery are desired.

SUMMARY

In a first aspect, methods of treating an eye of a patient following LASIK refractive surgery are provided, the eye comprising a cornea having an anterior surface, an ablated stroma, and a flap having an anterior surface, the flap surrounded by epithelium and a sclera, the ablated stroma providing the anterior surface of the flap a post-ablation profile when the flap is disposed on the ablated stroma, the method comprising: providing a covering comprising: an inner portion characterized by an inner rigidity, and comprising an upper surface and a lower surface; and an outer portion characterized by an outer rigidity, and comprising an upper surface and a lower surface; wherein the inner rigidity is greater than the outer rigidity; applying the covering against the eye so that the covering flexes with the lower surface of the inner portion disposed along the anterior surface of the flap and partially conforming to the post-ablation profile of the anterior surface; and resisting movement of the inner portion relative to the flap by engaging the lower surface of the outer portion with the eye along the epithelium, the sclera, or a combination thereof.

In a second aspect, methods of treating an eye of a patient following LASIK are provided, the eye comprising a cornea comprising an anterior surface, an ablated stroma, an epithelium, and a sclera, the ablated stroma characterized by a post-ablation profile, the method comprising: providing a covering comprising: an inner portion comprising a first lower surface characterized by at least one inner radius of curvature, wherein the at least one inner radius of curvature comprises a radius of curvature less than a radius of curvature of the post-ablation profile of the anterior surface of the cornea, wherein the inner portion is characterized by a substantially uniform thickness; and an outer portion comprising a second lower surface characterized by at least one outer radius of curvature; and applying the covering against the eye so that the covering flexes, with the inner portion at least partially disposed along and deforming so that an upper surface of the inner portion opposite the first lower surface of the inner portion optically conforms to the anterior surface of the cornea and at least a part of the outer portion engages the eye along the epithelium, the sclera, or a combination thereof.

In a third aspect, coverings for treating an eye following LASIK surgery are provided, comprising: an inner portion having an inner rigidity and at least one inner radius of curvature; and an outer portion having an outer rigidity and at least one outer radius of curvature; wherein the inner rigidity is greater than the outer rigidity; the inner radius of curvature is flatter than an inner portion of a cornea to which the covering is to be applied; and the at least one outer rigidity curvature is from 0D to 3.0D flatter than an at least one outer portion of a cornea to which the covering is to be applied.

BRIEF DESCRIPTION OF THE DRAWINGS

The drawings described herein are for illustration purposes only. The drawings are not intended to limit the scope of the present disclosure.

Reference is now made in detail to embodiments of the present disclosure. While certain embodiments of the present disclosure are described, it will be understood that it is not intended to limit the embodiments of the present disclosure to the disclosed embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

As used herein, a covering refers to an ophthalmic device that covers an eye of a patient and that may or may not provide refractive vision correction.

As used herein, an on-K fit of a covering encompasses fitting a covering to the flattest meridian of the cornea and the on-K fit can be flatter than the flattest meridian within about 1.5D. For example, for a cornea having keratometer values (K-value) of about 44D axis 90 and 43D axis 180, the on-K fit provides a covering having a curvature corresponding to an optical power within a range from about 43D to about 41.5D for the region of the eye measured. The on-K fit as described herein can allow for faster visual recovery and for minimization of discomfort following refractive surgery.

The optical power of the cornea in Diopters (D) can be related to the radius of curvature R with the formula $D=(1.3375-1)/R$, where 1.3375 corresponds to the index of refraction of the aqueous humor and R corresponds to the radius of curvature of the cornea. The curvature of the cornea is inversely related to the radius of curvature R such that as the radius of curvature increases the curvature of the cornea decreases and such that as the radius of curvature decreases the curvature of the cornea increases.

Figure 1:
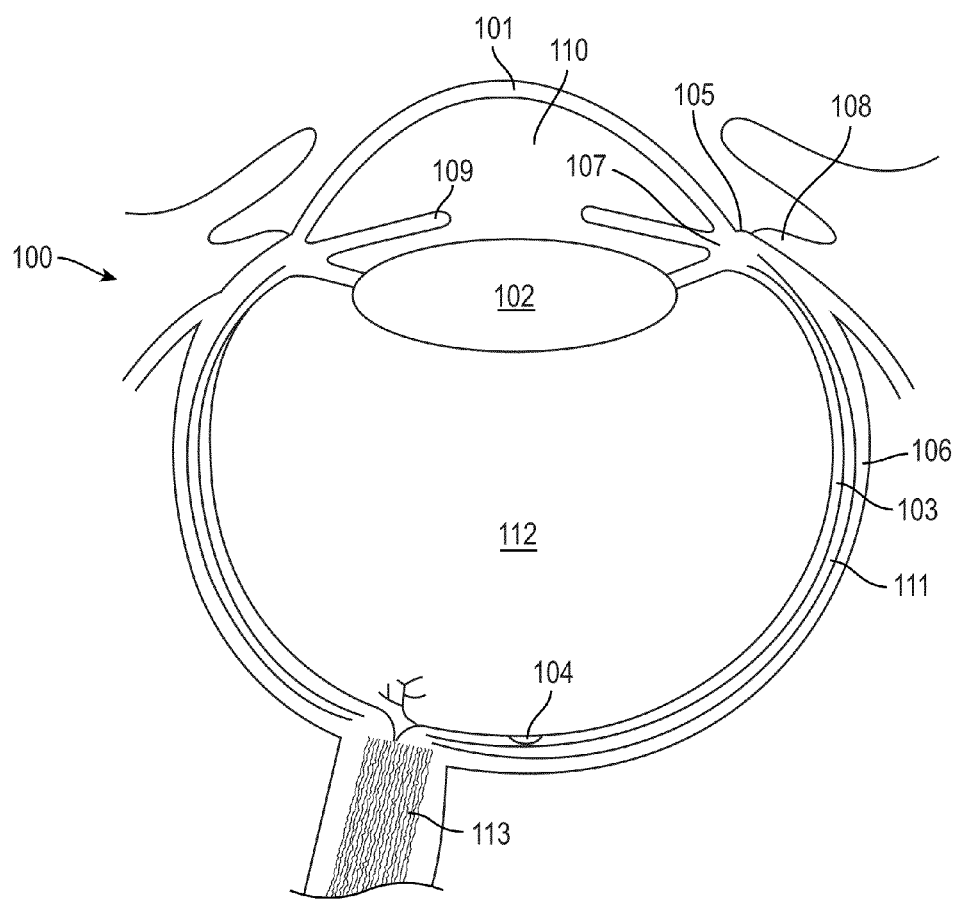
FIG. 1 shows a cross-section of a human eye.

FIG. 1 shows a cross-section of a human eye 100. The eye has a cornea 101 and a lens 102 configured to form an image on the retina 103, and the image can form on a fovea 104 corresponding to high visual acuity. The cornea 101 can extend to a limbus 105 of the eye, and the limbus 105 can connect to a sclera 106 of the eye. The eye 100 has a pars plana 107 located near limbus 105. A conjunctiva 108 of the eye can be disposed over the sclera 106. The lens 102 can accommodate to focus on an object seen by a patient. The eye has an iris 109 that defines a pupil 110 that may expand and contract in response to light. The eye also comprises a choroid 111 disposed between the sclera 106 and the retina 103. The eye has a vitreous humor 112 extending between the lens 102 and the retina 103. The retina 103 senses light of an image and converts the light image to neural pulses that are processed and transmitted along an optic nerve 113 onto the brain of the patient.

LASIK is a surgical procedure used to correct refractive vision errors such a myopia, hyperopia, and astigmatism in which a laser is used to reshape the cornea in order to improve visual acuity, e.g., the clearness and sharpness of an image. The LASIK procedure involves both a surgical cutting and laser sculpting of the cornea. During LASIK, the eye is immobilized by application of a soft corneal suction ring. A flap in the outer cornea is then created using a blade or laser leaving a hinge on one end of the flap. The flap is then folded back to expose the stroma, or middle section of the cornea. A laser is then used to vaporize the corneal stroma to remove tissue to reshape the cornea to correct vision. After the stromal layer is reshaped, the flap is repositioned over the eye and remains in position by natural adhesion. Optimal visual acuity is usually achieved within about 24 hours following surgery.

Figure 2:
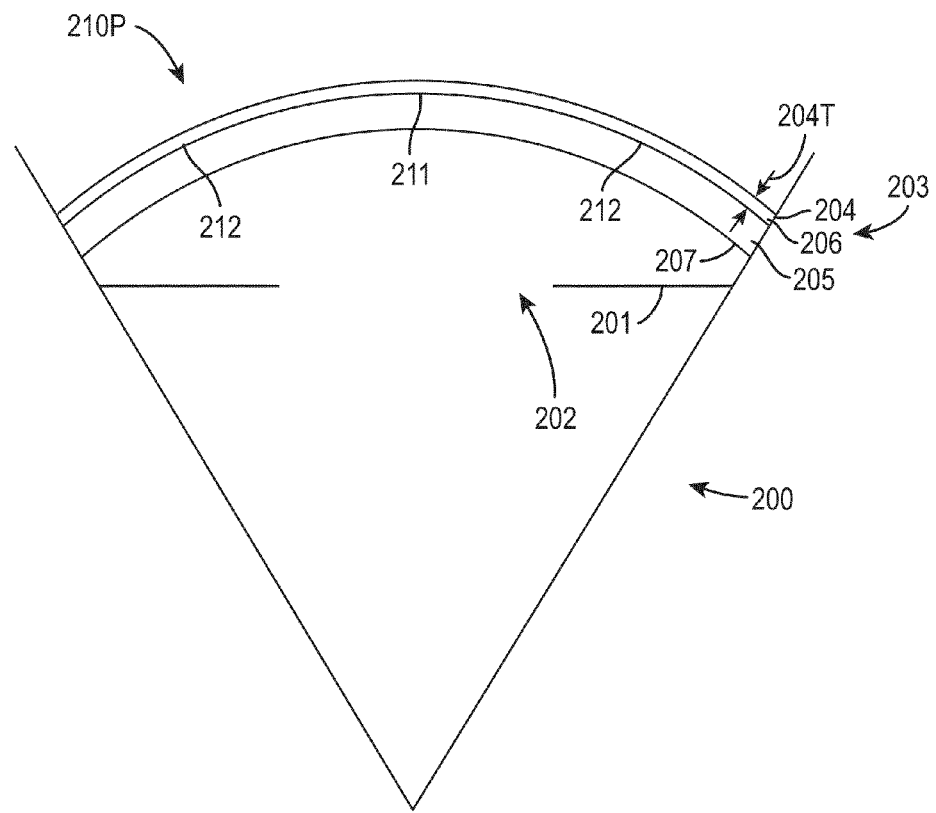
FIG. 2 shows a cross-section of a portion of an eye prior to photorefractive surgery.

FIG. 2 shows a cross-section of an eye before refractive surgery. The eye 200 comprises an iris 201 that defines a pupil 202, through which light passes such that the patient can see. Cornea 203 includes an epithelium 204 disposed over a stroma 205. The epithelium 204 comprises a thickness 204T that can be about 50 μm. A tear liquid covers the anterior surface of epithelium 204. In at least humans, primates and some birds, a Bowman's membrane 206 is disposed between epithelium 204 and stroma 205. Bowman's membrane 206 comprises an acellular substantially collagenous tissue with a thickness of about 5 μm to 10 μm. Stroma 205 comprises a substantially collagenous tissue with keratocytes disposed therein. In some animals, Bowman's membrane may be absent and the epithelium may be disposed adjacent to the stromal layer. An endothelium 207 is disposed under stroma 205. Endothelium 207 comprises a layer of cells that pump water from cornea 203 toward iris 201. The anterior surface of the cornea 203 including stroma 205 and epithelium 204 define an unablated profile 210P. In refractive surgery the center portion 211 of the profile 210P and bounded by portions 212 is sculpted to correct refractive vision errors.

The first step in the LASIK procedure is to slice the cornea from the side to produce a corneal flap that includes the epithelium and a portion of the stroma. The flap is cut using a device called a microkeratome. A part of the microkeratome flattens the cornea during the slice so as to create a corneal flap of uniform thickness. The slice is completed before a complete disk is created, which results in a corneal flap of uniform thickness with a hinge at one edge. The surgeon then rolls the flap back to expose an inner portion of the cornea. With the flap folded back, the surgeon performs the refractive correction on the inner portion of the cornea using a laser, such as an excimer laser. When the corneal sculpting is complete, the flap is repositioned into its original position and the procedure is complete. The eye has a natural suction facility that typically retains the flap in place when repositioned on the cornea.

Figure 3:
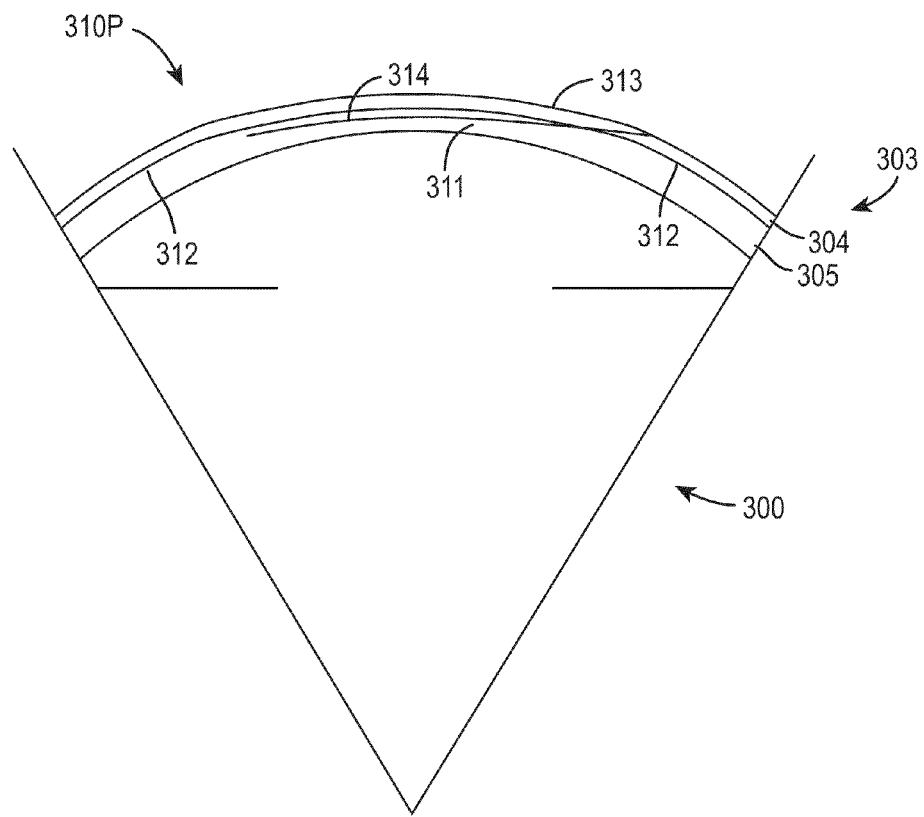
FIG. 3 shows a cross-section of a portion of an eye following LASIK.

FIG. 3 shows the portion of the eye 300 illustrated in FIG. 2 following LASIK. Following LASIK the center portion 311 of the stroma 305 has been sculpted as indicated by the thinner center thickness and flap 313 including incision 314 and the center portion of the cornea 303 including stroma 305 and epithelium 303 are repositioned and conform to the portion of the ablated stroma 305. The ablated stoma is characterized by an ablated profile 310P and bounded by unablated outer portions 312.

Although the LASIK surgical procedure is widely used, certain aspects of the procedure occasionally give rise to complications. For example, the formation of the corneal flap is one aspect of the overall LASIK procedure which can give rise to complications. Specifically, the formation of the corneal flap can result in epithelial abrasions or other damage due to the microkeratome blade, and the cut or incision by means of the microkeratome blade can sometimes be unpredictable. Moreover, in some patients, corneal haze or edema subsequent to surgery and flap wrinkles or curled flap edges have been attributed to problems in forming the corneal flap with the microkeratome. The failure of the flap to reseal following surgery is also a significant complication, because such failure creates a greater risk of infection and may adversely affect visual acuity.

Figure 5:
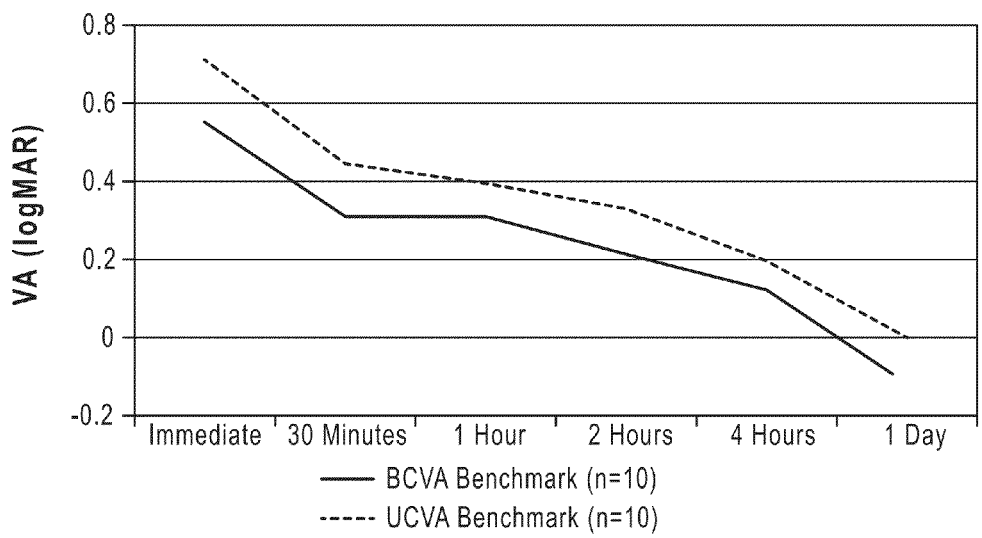
FIG. 5 is a graph showing the improvement in the uncorrected visual acuity (UCVA) and the best corrected visual acuity (BCVA) with time following LASIK surgery.
Figure 6:
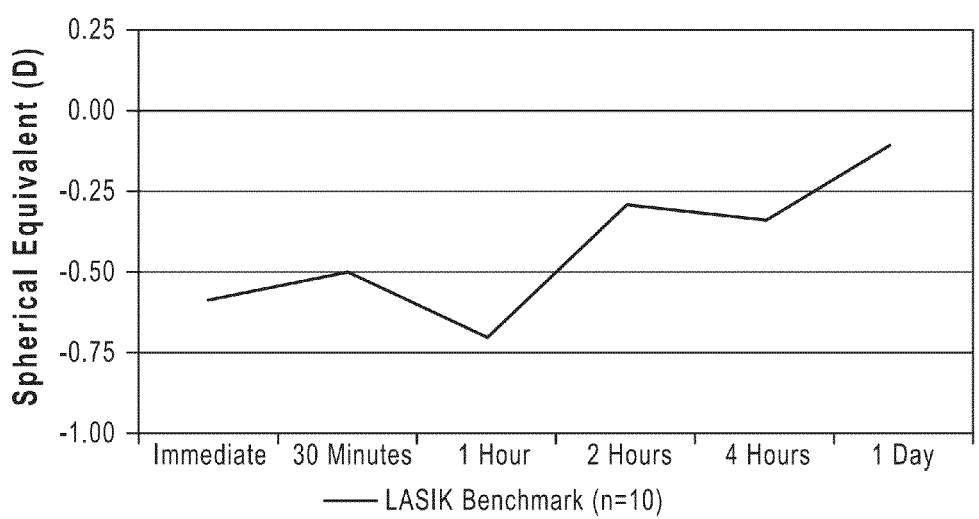
FIG. 6 is a graph showing the change in the refractive vision component with time following LASIK surgery.

An optimal level of vision, e.g., 20/20 vision, is typically achieved within about 24 hour following LASIK surgery. Suboptimal vision can manifest as a myopic refractive error immediately following LASIK surgery, which gradually diminishes during the first 24 hours. This phenomena is shown in FIG. 5 and FIG. 6. FIG. 5 shows the uncorrected visual acuity (UCVA) and best corrected visual acuity (BCVA) during the first 24 hours following LASIK surgery. Immediately following LASIK, a refractive correction of about 0.5 D can be required to correct vision, which decreases to about 0.05 D within the first about 4 hours. In FIG. 6, the refractive change (spherical equivalent, SE) is shown following LASIK surgery. It is believed that the refractive error is caused by steepening of the corneal curvature due to edema. Optical irregularities of the flap may in turn cause high order aberrations and/or the formation of an opaque bubble layer, which results in the BCVA not being 20/20 or better during the first few hours following surgery.

Figures 7A, 7B:
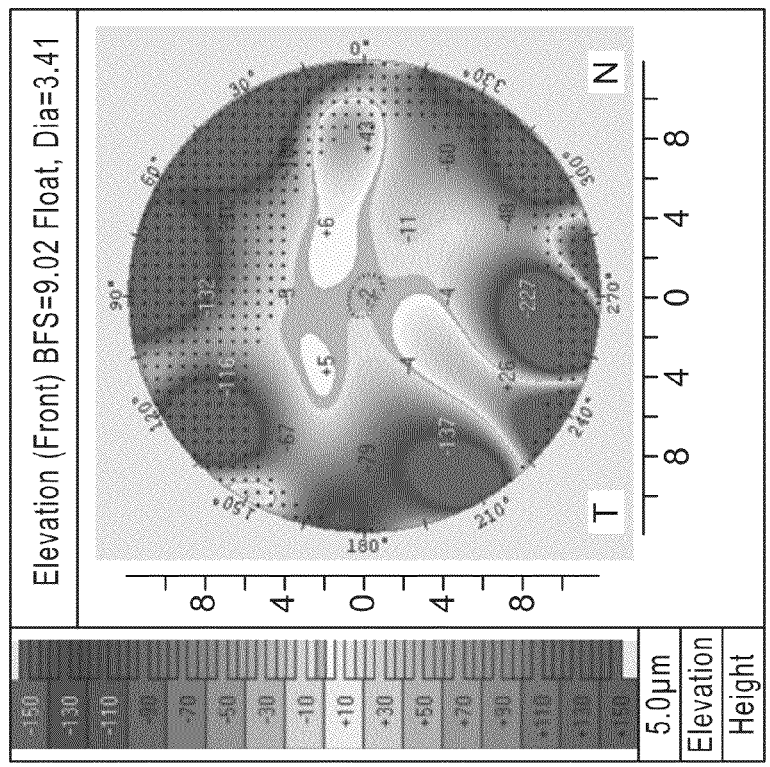
FIG. 7A shows a plot of the sagittal curvature of a cornea following LASIK surgery measured using a corneal topographer.
FIG. 7B shows the elevation profile of a cornea following LASIK surgery measured using a corneal topographer.

FIG. 7A and FIG. 7B illustrate the optical irregularities of a cornea following LASIK as measured using a corneal topographer.

Figure 8A:
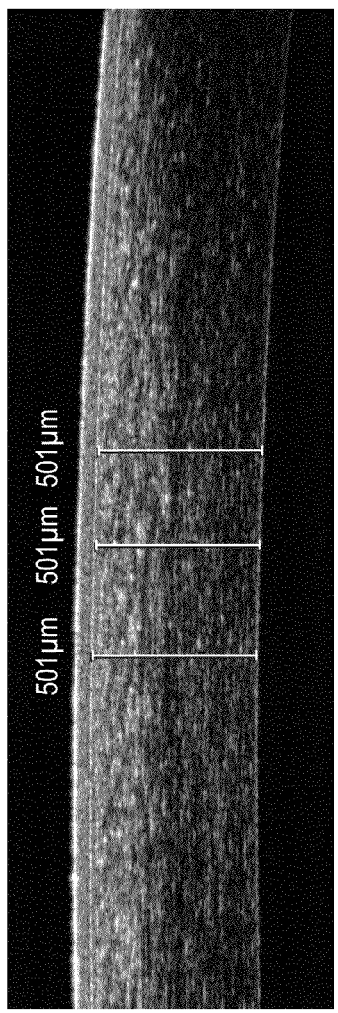
FIG. 8A shows a cross-sectional view of a cornea before LASIK surgery.
Figure 8B:
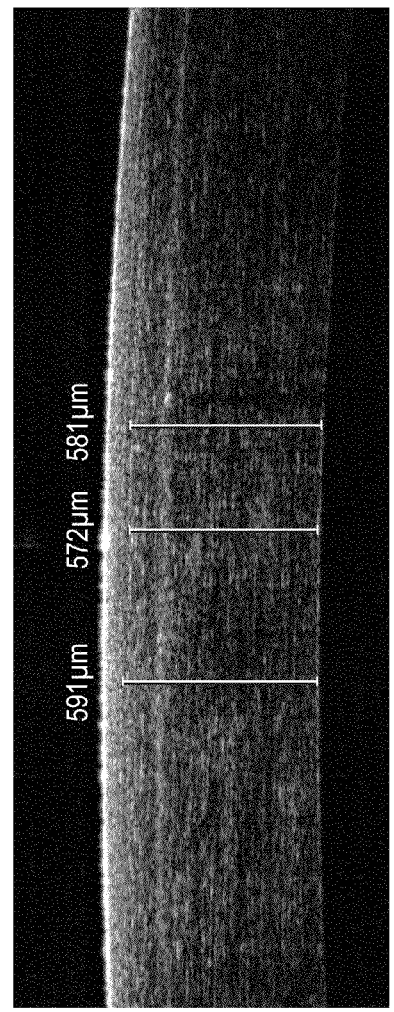
FIG. 8B shows a cross-sectional view of a cornea following LASIK surgery.

The effects of post-LASIK edema of stromal tissue is illustrated in FIG. 8A and FIG. 8B. A cross-sectional view of the stroma prior to LASIK is shown in FIG. 8A. The thickness of the stroma across the profile is 501 μm. LASIK surgery was then performed with a 120 μm interlase flap and the stroma was ablated to a depth of 42 μm across the section. As shown in FIG. 8B, edema causes the stroma to swell to a thickness from 572 μm to 591 μm across the same stromal section after the 42 μm ablation. The edema results in optical scattering, which manifests to a patient as halos around objects.

The combined effects of edema and optical defects result in suboptimal visual acuity following LASIK. Although vision improves dramatically during the first four hours following surgery and reaches an optimal post-operative state within 24 hours for the majority of patients, it is desirable that vision be restored as soon as possible after a LASIK procedure to enable patients to normally function.

When applied to an eye following LASIK surgery, coverings provided by the present disclosure improve visual acuity immediately following the surgical procedure, increase the rate at which optimal visual acuity is achieved, and reduce patient discomfort compared to recovery without wearing the covering.

Figure 9:
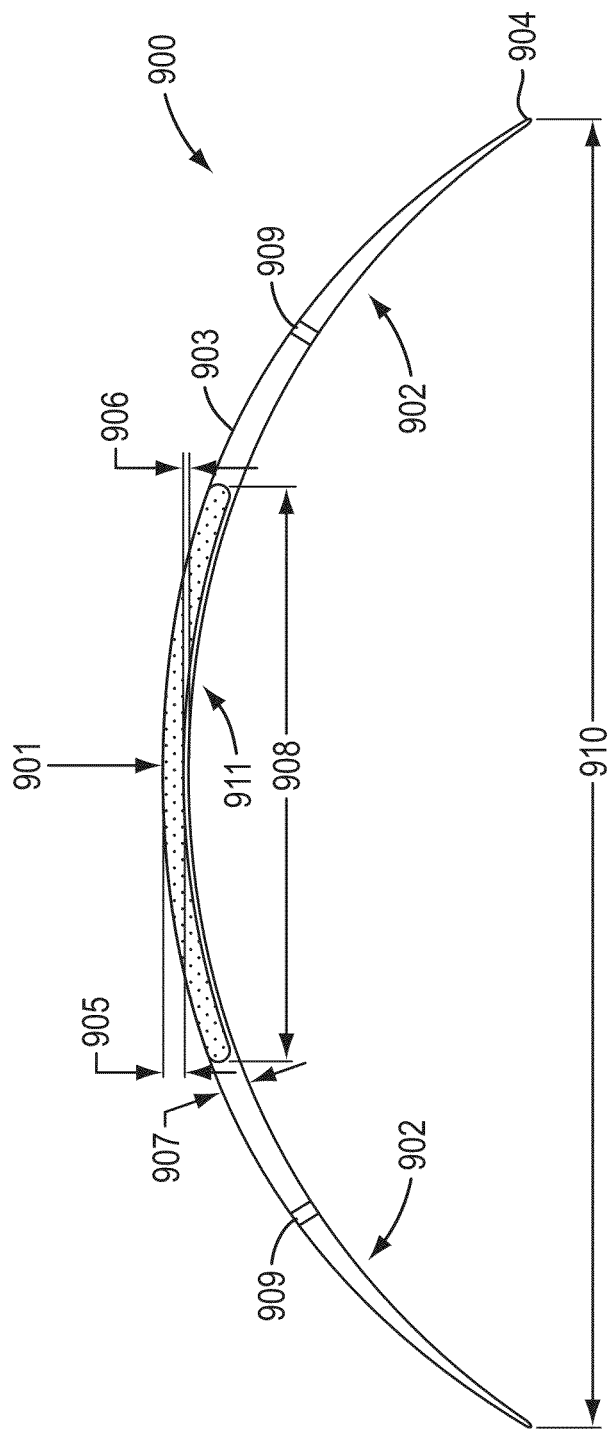
FIG. 9 shows a cross-sectional view of a covering according to certain embodiments of the present disclosure.

Certain embodiments provided by the present disclosure include coverings comprising an optical component and a coupling component, the optical component having a first rigidity, and the coupling component having a second rigidity, wherein the first rigidity is greater than the second rigidity. FIG. 9 shows covering 900, comprising optical component 901 and coupling component 902. Optical component 901 is also referred to herein as the inner portion and the coupling component 902 as the outer portion. The patient sees through the optical component.

The inner portion is configured to conform to the cornea of the patient when applied to the eye. The inner portion may comprise one or more materials of the same or different thicknesses each material having the same or different modulus. In certain embodiments, the inner portion comprises a single material that is substantially homogeneous throughout the thickness. In certain embodiments, the inner portion comprises a first material that extends along the inner surface of the inner portion and contacts the outer surface of the cornea, and a second material anterior to the first material. In such embodiments, the first material can be relatively thin, have a lower modulus than the second material, and can be configured to provide comfort. The second material can have a modulus that is greater than that of the first material and can be configured to provide proper function of the covering and in certain embodiments, to correct vision.

The inner portion may or may not provide vision correction. In certain embodiments in which the inner portion does not provide vision correction, the inner portion can be characterized by a substantially uniform thickness and may be characterized by a refractive index that is substantially the same as that of the cornea. In other embodiments, the inner portion can be characterized by a shape having a spheric shape or an aspheric shape. A suitable shape can be selected determined on the degree and type of vision correction desired. Certain embodiments in which the inner portion is configured to correct refractive error, the inner portion may be characterized by a refractive index that is not substantially the same as the refractive index of the cornea.

The inner portion has an inner surface that contacts the cornea. In certain embodiments, the inner portion is characterized by at least one inner radius of curvature such as one radius of curvature, two radii of curvature, or more than two radii of curvature. In certain embodiments, the at least one inner radius of curvature comprises a radius of curvature corresponds to or is less than that associated with the optical power of the ablated stroma. In certain embodiments the inner portion comprises at least one inner radius of curvature that is equal to or flatter than the post-ablation profile of the cornea so that applying the covering comprises decreasing the at least one inner radius of curvature along the inner surface of the inner portion. In certain embodiments, the at least one inner radius of curvature is flatter than the post-ablation profile of the cornea by about 0D to about 3D.

Figure 4A:
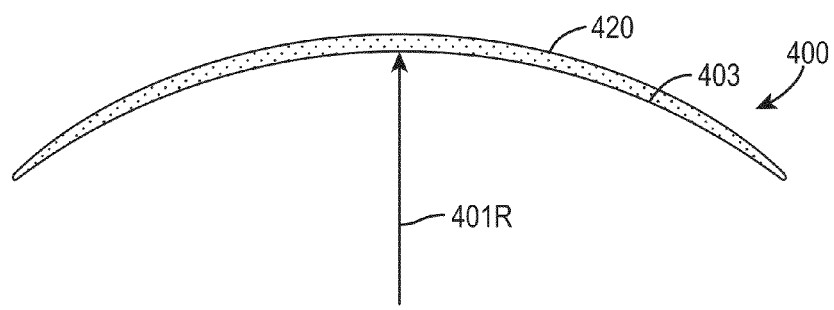
FIG. 4A shows a cross-section of a simplified covering provided by the present disclosure.
Figure 4B:
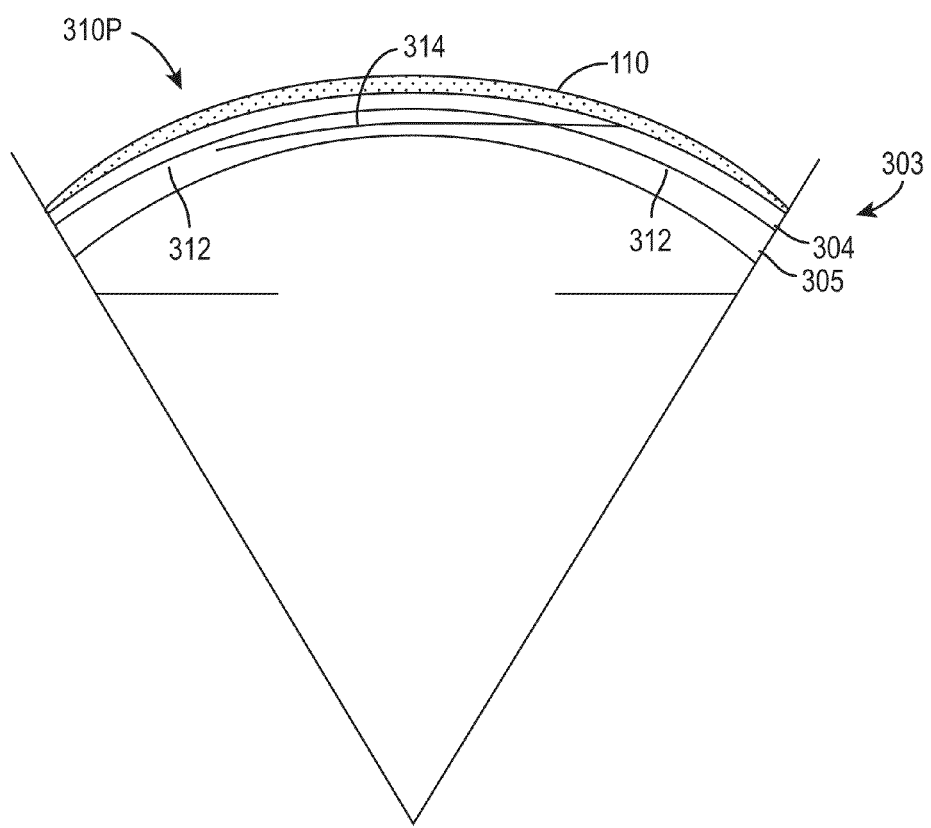
FIG. 4B shows a cross-section of the covering shown in FIG. 4A applied to the portion of the eye shown in FIG. 3.

When a covering is applied to an eye of a patient following LASIK, the inner portion deforms or flexes to substantially conform to the surface of the cornea having an ablated profile. This is shown in FIG. 4A and FIG. 4B. FIG. 4A shows a simplified cross-section of a cornea 400 in which the inner surface is characterized by a radius of curvature 401R. When applied on an ablated cornea following LASIK surgery, such as the ablated cornea shown in FIG. 3, the inner surface of the covering 400 conforms to the anterior surface of the cornea, which is characterized by a post-ablation profile. During application, the covering flexes such that the inner surface of the covering flattens, e.g., the radius of curvature of the inner portion increases and then takes the shape of the ablated corneal profile. In FIG. 4B, the shape of the inner surface of the covering prior to application to the cornea is illustrated by the dashed line.

In certain embodiments, the index of refraction of the inner portion is substantially the same as the index of refraction of the cornea. In embodiments in which the inner portion provides for vision correction, the refractive index of the inner portion may be different than that of the cornea such as greater than the refractive index of the cornea or less than the refractive index of the cornea.

The outer portion is generally configured to at least partially conform to the surface of the cornea and the peripheral portion or edge of the outer portion is configured to engage the epithelium, the sclera, or a combination thereof, so as to resist movement of the inner portion when the covering is placed on the eye.

In certain embodiments, the at least one inner radius of curvature comprises a radius of curvature corresponds to or is less than that associated with the optical power of the ablated stroma; and the method further comprises deforming the inner portion during the applying of the covering so that the upper surface of the inner portion optically conforms to the anterior surface of the flap such that patient vision through the covering benefits from the post-ablation profile and so as to modify tissue response of the cornea to the LASIK surgery such that, within 4 hours of the LASIK surgery, patient discomfort associated with the LASIK surgery is mitigated and/or patient vision associated with the LASIK surgery is enhanced.

In certain embodiments, the at least one inner radius of curvature corresponds to or is flatter than the post-ablation profile of the cornea, so that applying the covering comprises decreasing the at least one inner radius of curvature along the inner surface of the inner portion of the covering.

In certain embodiments, the at least one inner radius of curvature is flatter than the post-ablation profile of the cornea by about 0D to about 3D; and the method further comprises deforming the inner portion during the applying of the covering so that the upper surface of the inner portion optically conforms to the anterior surface of the flap such that patient vision through the covering benefits from the post-ablation profile and so as to modify tissue response of the cornea to the LASIK surgery such that, within 4 hours of the LASIK surgery, patient discomfort associated with the LASIK surgery is mitigated and/or patient vision associated with the LASIK surgery is enhanced.

In certain embodiments, the outer portion comprises at least one intermediate portion and a peripheral portion. The at least one intermediate portion is configured to at least partially conform to the cornea and the peripheral portion is configured to engage the eye so as to prevent movement of the inner portion. Both the at least one intermediate portion and the peripheral portion are configured to flex or deform when applied to an eye of the patient.

The inner surface of each of the at least one intermediate portions may independently be characterized by at least one radius of curvature. The radius of curvature defining each of the intermediate portions may have a focus at a point along the central axis of the covering (on-axis) or may have a focus off the central axis of the covering (off-axis). In certain embodiments, a covering may have from one to six intermediate portions, from two to six intermediate portions, or from four to six intermediate portions where each of the intermediate portions is characterized by a different radius of curvature. In certain embodiments, a covering comprises one intermediate portion, two intermediate portions, three intermediate portions, four intermediate portions, five intermediate portions, or six intermediate portions.

The peripheral portion also comprises a lower surface characterized by at least one radius of curvature. The shape of the lower surface of the peripheral portion of the covering is configured to deform or flex to engage the outer portion of the eye along the epithelium, the sclera, or a combination thereof to resist movement of the inner portion. For use in LASIK applications, the peripheral portion and to a certain extent the at least one intermediate portion is configured to engage the LASIK flap so as to hold the LASIK flap against the cornea and thereby promote healing.

The rigidity of the inner portion is greater than the rigidity of the outer portion. For example, in certain embodiments, a covering can have an inner rigidity from about $1.2E^{-6}$ Pa-m$^3$ to about $3.1E^{-3}$ Pa-m$^3$, from about $1E^{-5}$ Pa-m$^3$ to about $1E^{-3}$ Pa-m$^3$, and in certain embodiments, from about $1E^{-4}$ Pa-m$^3$ to about $1E^{-3}$ Pa-m$^3$.

In certain embodiments, a covering can have an outer rigidity from about $5.4E^{-9}$ Pa-m$^3$ to about $1.5E^{-4}$ Pa-m$^3$, from about $1E^{-8}$ Pa-m$^3$ to about $1E^{-4}$ Pa-m$^3$, from about $1E^{-7}$ Pa-m$^3$ to about $1E^{-5}$ Pa-m$^3$, and in certain embodiments, from about $1E^{-6}$ Pa-m$^3$ to about $1E^{-5}$ Pa-m$^3$.

The rigidity of a portion of the covering can be increased by increasing the thickness of a single material, using a material having a higher modulus for the same thickness, or by combining materials having different moduli and thicknesses.

The rigidity of a portion of a covering is approximated by the modulus of the material comprising the portion multiplied by the cube of the thickness. When a portion comprises more than one material, the rigidity can be approximated based on the average modulus of the portion multiplied by the thickness cubed of the portion. For example, a portion comprising a first material with a modulus of 20 MPa and a thickness of 90 µm and a second material with a modulus of 5 MPa and a thickness of 10 µm will have an average modulus of 18.5 MPa. The rigidity of the portion can then be approximated by multiplying the average modulus times the cube of the thickness, which for the present example is determined to be $18.5E^{-6}$ Pa-m$^3$. Although these calculations can be based on approximations, a person of ordinary skill in the art can conduct simulations, for example finite element modeling simulations, so as to more accurately estimate relative rigidity and/or measure pressures and deflection forces and pressures to determine rigidities of the various portions of the covering.

In certain embodiments, the inner portion is further characterized by an index of refraction that may correspond substantially to the index of refraction of the cornea, for example the index of refraction may be within a range from about 1.38 to about 1.43 so as to match the index of refraction of the cornea to within about +/−0.05.

In certain embodiments, for example, where the covering provides vision correction, the inner portion may be characterized by an index of refraction that is different than the refractive index of the cornea.

Referring to FIG. 9, in certain embodiments, covering 900 has a diameter 910 from about 9 mm to about 16 mm, in certain embodiments, from about 10 mm to about 15 mm, and in certain embodiments, from about 12 mm to about 14 mm. In certain embodiments, optical component 901 comprises a center thickness from about 100 µm to about 500 µm, from about 200 µm to about 400 µm, and in certain embodiments, from about 250 µm to about 350 µm.

In certain embodiments, inner portion 901 comprises a first material having a first thickness 905 and a second material having a second thickness 903. In such embodiments, the second material may be disposed on the inner surface of inner portion 901, e.g., the surface facing the cornea, and may be the same material as the material forming outer portion 902. The second material may have a thickness 903 from about 5 µm to about 60 µm, from about 10 µm to about 50 µm, and in certain embodiments, from about 20 µm to about 40 µm. In such embodiments, where inner portion 901 comprises two materials, the total thickness of the optical component may be from about 100 µm to about 550 µm, from about 200 µm to about 450 µm, and in certain embodiments, from about 250 µm to about 350 µm.

In certain embodiments, inner portion 501 comprises an optically clear material having a modulus from about 10 MPa to about 70 MPa, from about 20 MPa to about 60 MPa, from about 20 MPa to about 50 MPa, and in certain embodiments from about 30 MPa to about 40 MPa.

In certain embodiments, the inner portion of a covering comprises a single material having a modulus from about 1.2 MPa to about 25 MPa, a thickness from about 100 µm to about 500 µm, and a rigidity from about $1.2E^{-6}$ Pa-m$^3$ to about $3.1E^{-3}$ Pa-m$^3$. In certain embodiments, the outer portion of a covering comprises a single material having a modulus from about 0.2 MPa to about 1.4 MPa, a thickness from about 30 µm to about 500 µm (e.g., tapering from the thickness of the inner portion), and a rigidity from about $5.4E^{-9}$ Pa-m$^3$ to about $1.5E^{-4}$ Pa-m$^3$. In certain embodiments, the inner portion of a covering comprises a single material having a modulus from about 1.2 MPa to about 25 MPa, a thickness from about 100 µm to about 500 µm, and a rigidity from about $1.2E^{-6}$ Pa-m$^3$ to about $3.1E^{-3}$ Pa-m$^3$; and the outer portion of a covering comprises a single material having a modulus from about 0.2 MPa to about 1.4 MPa, a thickness from about 30 µm to about 500 µm (e.g., tapering from the thickness of the inner portion), and a rigidity from about $5.4E^{-9}$ Pa-m$^3$ to about $1.5E^{-4}$ Pa-m$^3$.

Referring to FIG. 9, inner portion 901 may be configured to correct vision or may not be configured to correct vision. For example, inner portion 901 may be characterized by a refractive index that is different than that of the cornea and/or may be spherically shaped, aspherically shaped, or may be another suitable shape that provides for vision correction. In such embodiments, the inner surface of the inner portion of a covering is configured to substantially conform to the ablated profile of the cornea of a patient's eye following LASIK surgery.

In certain embodiments, inner portion 901 comprises a material selected from silicone, silicone hydrogel, and a combination thereof. In certain embodiments, optical component 901 comprises silicone, in certain embodiments, silicone hydrogel, and in certain embodiments a combination of silicone and silicone hydrogel.

In certain embodiments, inner portion 901 comprises a center thickness from about 150 μm to about 500 μm, a diameter from about 3 mm to about 9 mm, a radius of curvature from about 7 mm to about 12 mm, and a modulus from about 20 MPa to about 50 MPa.

In certain embodiments, outer portion 902 extends from inner portion 901 to an outer periphery 904, where the thickness at the juncture with inner portion 901 is the same as or similar to that of outer portion 902, and gradually tapers toward outer periphery 904, wherein the thickness of the coupling component at the periphery is from about 5 μm to about 60 μm, from about 10 μm to about 50 μm, and in certain embodiments, from about 20 μm to about 40 μm.

In certain embodiments, outer portion 902 comprises at least one radius of curvature 512. For example, in certain embodiments, outer portion 902 comprises a single radius of curvature, and in certain embodiments, outer portion 902 comprises more than one radius of curvature such as two, three, four, five, six, or more than six radii of curvature. The at least one radius of curvature can be, for example, from about 5 mm to about 15 mm, from about 6 mm to about 13 mm, from about 7 mm to about 12 mm, and in certain embodiments, from about 6 mm to about 10 mm. The one or more radius of curvature 912 characterizing outer portion 902 is less than the radius of curvature of inner portion 901.

Figure 10:
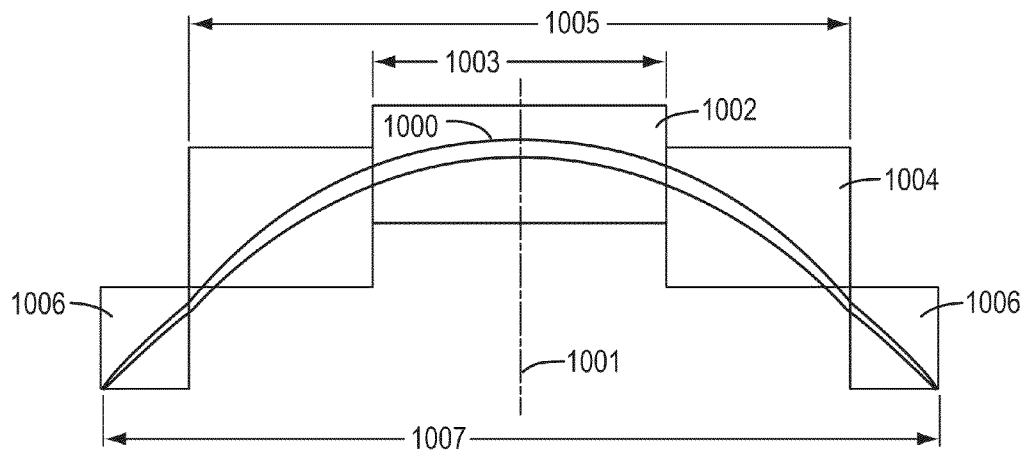
FIG. 10 shows a cross-sectional view of a covering according to certain embodiments of the present disclosure.

FIG. 10 shows a cross-section view of a covering according to certain embodiments of the present invention. The covering shown in FIG. 10 has a least a tri-curve profile including a central curvature, a mid-periphery curvature and a peripheral curvature. The central curvature refers to the curvature of the inner portion of the covering spanning an approximately 3 mm diameter region in the center of the covering. The mid-periphery curvature refers to the curvature in a radial region about 5 mm from the center of the covering. The peripheral curvature refers to the curvature toward the edge of the covering. In certain embodiments, as shown for example in FIG. 10, the transition from the peripheral curvature region to other parts of the covering may not be smooth and may be characterized by an angle. FIG. 10 shows a centerline 1001 of coverings 1000 provided by the present disclosure, having a central region 1002 and mid-peripheral regions 1004 on either side of the central region 1002. In certain embodiments, the diameter 1003 of central region 1002 is from about 5 mm to about 7 mm, from about 5.5 mm to about 6.5 mm, and in certain embodiments is about 6 mm. In certain embodiments, the mid-peripheral regions 1004 extend form the edge diameter of center region 1002 to about 5 mm from centerline 1001. Accordingly, the diameter of the mid-peripheral region can be from about 7 mm to about 11 mm, from about 7 mm to about 10 mm, from about 6.5 mm to about 11 mm, from about 6.5 mm to about 10 mm, and in certain embodiments, from about 6 mm to about 10 mm. In certain embodiments, the peripheral diameter 1007 of a covering can be from about 11 mm to about 16 mm, from about 12 mm to about 15 mm, and in certain embodiments, about 14 mm. As referred to herein, the outer portion comprises the mid-peripheral regions, which are also referred to as intermediate portions, and the peripheral portion.

Referring to FIG. 9, in certain embodiments, outer portion 902 comprises a material having a modulus from about 0.05 MPa to about 4 MPa, from about 0.1 MPa to about 3 MPa, from about 0.1 MPa to about 2 MPa, and in certain embodiment from about 0.2 MPa to about 1.5 MPa.

In certain embodiments, outer portion 902 comprises a material selected from silicone, silicone hydrogel, and a combination thereof. In certain embodiments, coupling component comprises silicone, in certain embodiments, silicone hydrogel, and in certain embodiments a combination of silicone and silicone hydrogel.

In certain embodiments, outer portion 902 does not include fenestrations. In other embodiments, outer portion 902 may comprise fenestrations.

In certain embodiments, outer portion 902 may comprise a thickness tapering from the thickness of inner portion 901 to a thickness of about 30 μm at the periphery 904 of the coupling component; a plurality or radius of curvature from about 7 mm to about 12 mm; and comprises a material having a modulus from about 0.1 MPa to about 2 MPa. In embodiments in which outer portion 902 comprises a plurality of radii of curvatures 912, the radius of curvature decreases from the optical component toward the periphery.

A covering, including inner portion 901 and outer portion 902, is configured to provide a seal to a tissue of an eye such as an epithelium to thereby resist movement of the optical component on an eye and to prevent fluid from getting under the covering, thereby enhancing edema recovery.

As disclosed herein, the inner portion comprises and inner surface characterized by at least one curvature, and the outer portion comprising an inner surface characterized by at least one of curvature. Furthermore, in certain embodiments, the outer portion comprises a peripheral portion characterized by a peripheral curvature, and at least one intermediate portion, each of the at least one intermediate portions independently characterized by an intermediate curvature. Each of the curvatures may be the same, each of the curvatures may be different, and in certain embodiments, at least some of the curvatures are the same. Furthermore, each of the curvatures may be spheric or aspheric. A spheric curvature can be characterized by a radius of curvature. An aspheric curvature encompasses a curvature that is not spheric.

In certain embodiments, the inner surface of a covering is characterized by at least one spheric curvature. In certain embodiments, the inner surface of a covering is characterized by at least one aspheric curvature. In certain embodiments, the inner surface of a covering is characterized by a combination of spheric curvatures and aspheric curvatures.

In certain embodiments, a radius of curvature may have a focus along an extension of the central axis of the covering. In certain embodiments, a radius of curvature may have a focus that is not located along an extension of the central axis of the covering. The extension of the central axis of the covering refers to a line segment extending from the center of the covering and projecting perpendicular to a plane defined by the peripheral edge of the covering.

In certain embodiments, the inner portion comprises an inner surface having a shape characterized by a single radius of curvature, by two radii of curvature, and in certain embodiments by three radii of curvature.

In certain embodiments, the outer portion of the covering comprises an inner surface characterized by a single radius of curvature, by two radii of curvature, by three radii of curvature, by four radii of curvature, by five radii of curvature, by six radii of curvature, or by more than six radii of curvature, such as from 8 to 10 radii of curvature or more. Thus, in certain embodiments the outer portion comprises an inner surface characterized from 1 to 6 radii of curvature, from 2 to 6 radii of curvature, and in certain embodiments, from 4 to 6 radii of curvature.

In general, the inner surface of the covering is configured to substantially conform to the anterior surface of the cornea. In certain embodiments, substantially conforming to the anterior surface of the cornea means that the inner portion of the covering and at least a portion of the outer portion of the covering physically contact the epithelium when the covering is applied to an eye of the patient. In certain embodiments in which the outer portion comprises a peripheral portion and at least one intermediate portion, the peripheral portion contacts the epithelium, sclera, or a combination thereof, and one or more of the intermediate portions may or may not contact the epithelium when the covering is applied to an eye of a patient.

Coverings provided by the present disclosure may have different cross-sectional shapes. For example, in certain embodiments, the inner portion may have a substantially uniform thickness, and the cross-sectional thickness of the covering may taper toward the periphery of the covering.

In certain embodiments, the inner portion is not intended to provide for vision correction and in such cases, the inner portion has a substantially uniform thickness. Such embodiments are suitable, for example, when LASIK provides adequate vision correction and additional correction is not necessary.

In certain embodiments, the inner portion may be characterized by a shape that provides vision correction. For example the inner portion may be characterized by a spheric or aspheric shape. In such embodiments, the outer surface of the inner portion may be characterized by a spheric or an aspheric profile.

In certain embodiments, the inner portion comprises a different material than the outer portion. In certain embodiments, the inner portion and the outer portion comprise the same material. In embodiments in which the inner portion and the outer portion comprise the same material, the different moduli may be realized by the detailed chemistry of the polymer used, such as different crosslinking densities.

In certain embodiments, the inner portion of a covering and the outer portion of the covering comprise a first material characterized by a first modulus and extending along a lower surface of the covering; and the inner portion comprises a second material characterized by a second modulus disposed anteriorly to the first material, the second modulus being greater than the first modulus. In such embodiments, the first material is a thin layer that is configured to promote comfort of the covering when applied to the cornea by cushioning between the anterior surface of the cornea and the layer of the first material. The second material is configured to promote a beneficial optical shape of an anterior surface of the applied covering over the eye.

The index of refraction of one or more layers of covering 100 may correspond substantially to the index of refraction of the cornea.

A covering may comprise one or more of many optically clear materials, for example synthetic materials or natural material such collagen-based materials, and combinations thereof, such as described in U.S. Publication No. US 2010-0036488. For example, a coverings material may comprise a naturally occurring material, such as collagen based material. Alternatively or in combination, a covering material may comprise a known synthetic material, for example hydroxyethyl methacrylate (HEMA) hydrogel, hydrogel, silicone, for example hydrated silicone and derivatives thereof. For example the optically clear material may comprise one or more of silicone, silicone hydrogel, silicone comprising resin, silicone comprising silicate, acrylate, collagen, or a combination of any of the foregoing. The cured silicone may comprise silicone that is two-part, heat-curable and RTV (room temperature vulcanized). For example, polydimethyl siloxane such as NuSil, or poly(dimethyl) (diphenyl) siloxane may be used to mold the covering, for example with less than 10% water content so as to increase oxygen diffusion through the covering. A covering may comprise perfluoropolyethers or fluorofocal. The material may comprise, for example, silicone elastomer having optically clear silicate disposed therein and a water content of no more than about 10%, for example no more than about 5%, such that the covering has a very high Dk exceeding 150, and the silicone lens comprising silicate can be treated to provide a wettable surface. A covering may comprise hydrogel, for example silicone hydrogel, and can be formed with a water content within a range from about 5% to about 35% and a modulus within a range or a combination of ranges from about 0.1 MPa to about 40 MPa, such that the covering conforms at least partially to the ablated stroma.

A covering may comprise silicone or silicone hydrogel having a low ionoporosity such that covering seals to the cornea. For example, covering may comprise silicone hydrogel comprising a low ion permeability, and the range of water can be from about 5% to about 35%, such that the Dk is 100 or more. In certain embodiments, the low ion permeability may comprise an Ionoton Ion Permeability Coefficient of no more than about $0.25 \times 10^{-3}$ cm$^2$/sec so as to seal the cornea, for example no more than about $0.08 \times 10^{-3}$ cm$^2$/sec. In certain embodiments, the low ion permeability comprises an Ionoton Ion Permeability Coefficient of no more than about $2.6 \times 10^{-6}$ mm$^2$/min to seal the cornea, for example no more than about $1.5 \times 10^{-6}$ mm$^2$/min.

A covering may comprise a wettable surface coating disposed on at least the upper side of the covering, such that the tear film of the patient is smooth over the covering and the patient can see. The wettable surface coating may comprise a lubricious coating for patient comfort, for example to lubricate the eye when the patient blinks. The wettable coating may comprise a contact angle no more than about 80 degrees. For example the coating may comprise a contact angle no more than about 70 degrees and the contact angle can be within a range from about 55 degrees to 65 degrees to provide a surface with a smooth tear layer for vision. For example, the wettable coating can be disposed both an upper surface and a lower surface of the covering. The upper surface may comprise the wettable coating extending over at least the inner portion of the covering.

A wettable coating may comprise one or more of many materials. For example, a wettable coating may comprise polyethylene glycol (PEG), and the PEG coating can be disposed on Parylene™. Alternatively, a wettable coating may comprise a plasma coating, and a plasma coating may comprise a luminous chemical vapor deposition (LCVD) film. For example, in certain embodiments a plasma coating comprises at least one of a hydrocarbon, for example $CH_4$, $O_2$ or fluorine containing hydrocarbon, for example $CF_4$ coating. Alternatively or in combination, a wettable coating may comprise a polyethylene glycol (PEG) coating or 2-hydroxyethyl-methacrylate (HEMA). For example, a wettable coating may comprise HEMA disposed on a Parylene™ coating, or a wettable coating may comprise N-vinylpyrrolidone (NVP) disposed on a Parylene™ coating.

Appropriate covering dimensions can be determined in many ways, for example with topography measurements of the cornea and sclera. Corneal and scleral topography can be measured with many instruments, such as with the Orbscan™ topography system commercially available from Bausch and Lomb, and the Pentacam™ Scheimpflug camera system commercially available from Oculus, and commercially available optical coherence tomography (OCT). The ablation profile can be combined with the topography to determine the shape of the eye.

The dimensions of a covering can be sized to one or more of the cornea and sclera based on tolerances that may be determined clinically.

To speed visual recovery following LASIK surgery, methods provided by the present disclosure comprise providing a covering to the eye of a patient immediately following refractive surgery.

A covering may be applied to the eye of a patient at any appropriate time following LASIK surgery, such as immediately after the flap is folded onto the ablated stroma, or shortly after the flap is folded onto the ablated stroma. A covering may be applied by approximately centering the covering on the cornea of a patient's eye and providing a slight pressure against the covering to flex the covering against the cornea such that the covering is retained against the cornea. The moduli of the materials and the shape of the inner surface of the covering from the center to the periphery of a covering are selected to enable the inner surface of the covering to conform to the surface of the cornea, to retain the covering against the cornea during normal wear, to immediately improve visual acuity, to speed the recovery of optimal visual acuity, and to enhance patient comfort.

Figure 11:
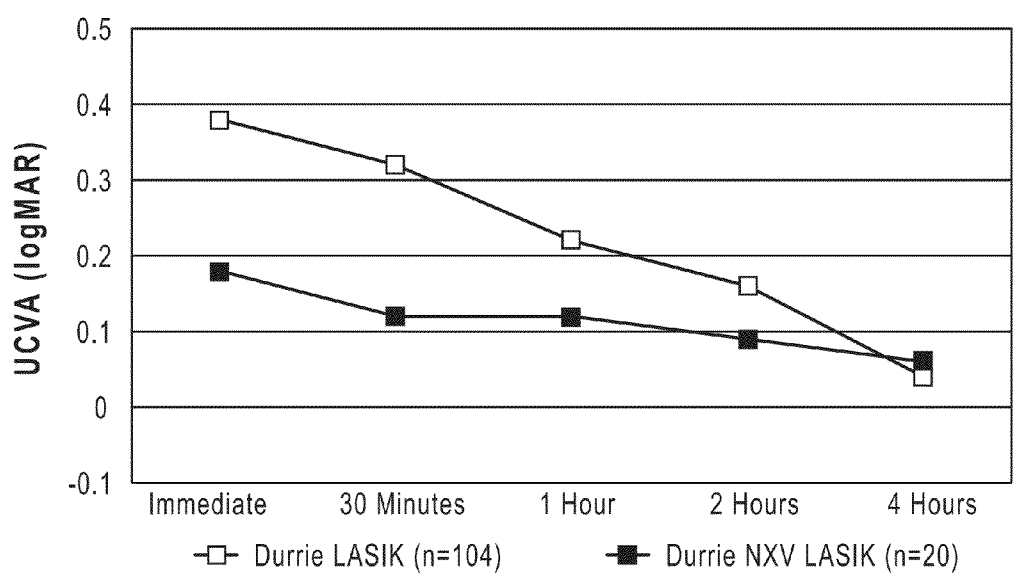
FIG. 11 is a graph of the monocular UCVA following LASIK surgery in a population of patients wearing a covering provided by the present disclosure (Durrie NXV LASIK) and in a population of patients without the covering (Durrie LASIK).

The improvement in visual recovery provided by methods of the present disclosure is shown in FIG. 11. In FIG. 11, the monocular UCVA is shown at various times following LASIK surgery. Without a covering applied to the eye, the UCVA is about 0.4 log MAR corresponding to about 20/50 vision immediately following LASIK and the UCVA gradually decreases toward 0 corresponding to 20/20 vision within the first 4 hours. In comparison, when a covering is applied following LASIK, the initial UCVA is about 0.2 log MAR corresponding to 20/32 vision, which gradually improves toward 20/20 vision over the next 4 hours. The ability of the covering to improve vision immediately following LASIK can be attributed to the ability of the covering to provide an optically smooth corneal surface.

Figure 12A:
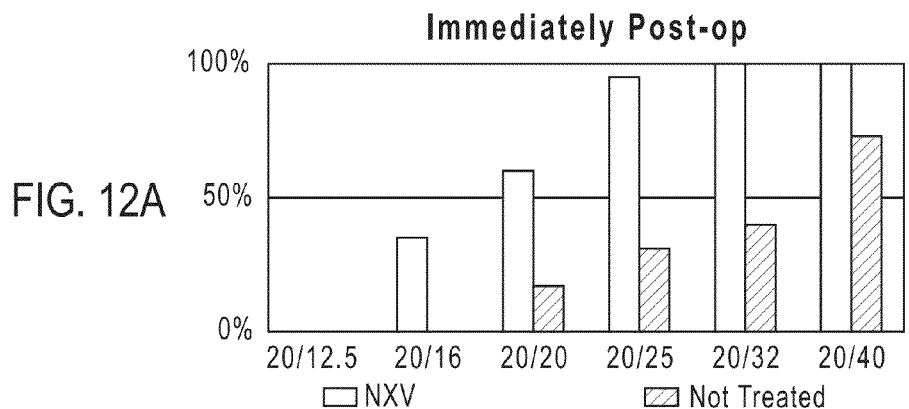
FIGS. 12A-12F are histograms showing the percent of patients having a certain visual acuity or better at various times following LASIK surgery. The visual acuity of a population of patients wearing a covering provided by the present disclosure (NXV) is compared to that of a population of patients not wearing a covering (not treated).
Figure 12B:
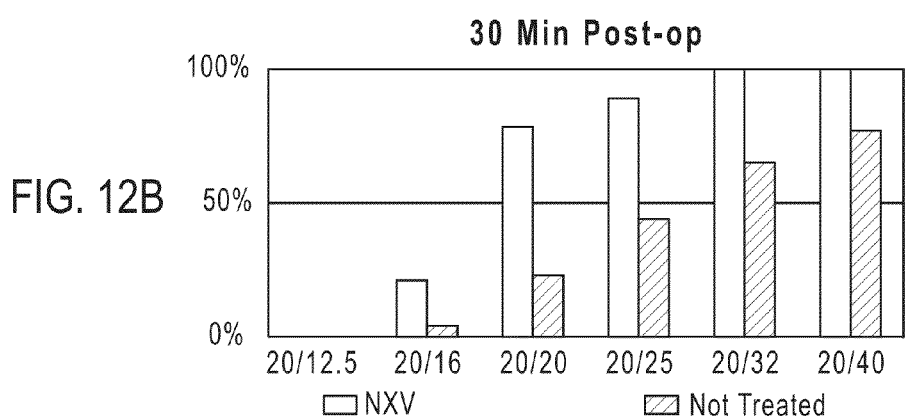
Figure 12C:
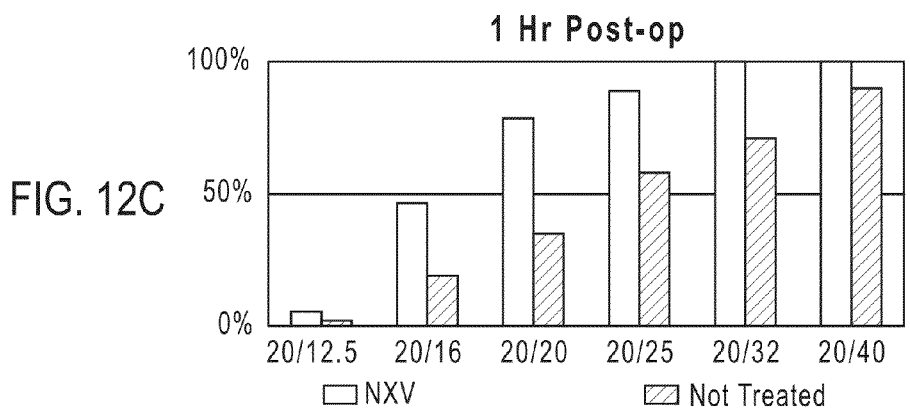
Figure 12D:
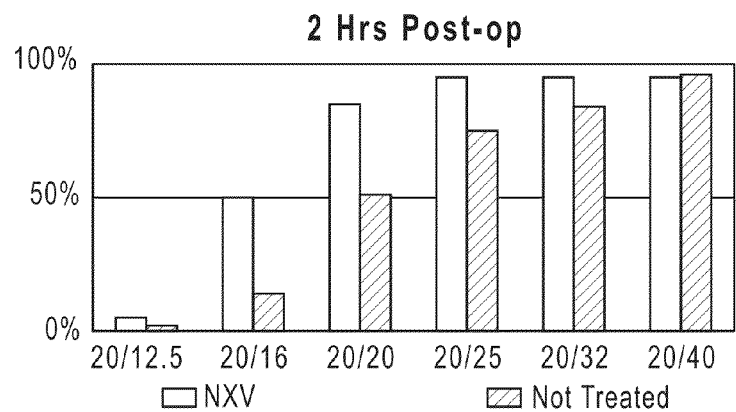
Figure 12E:
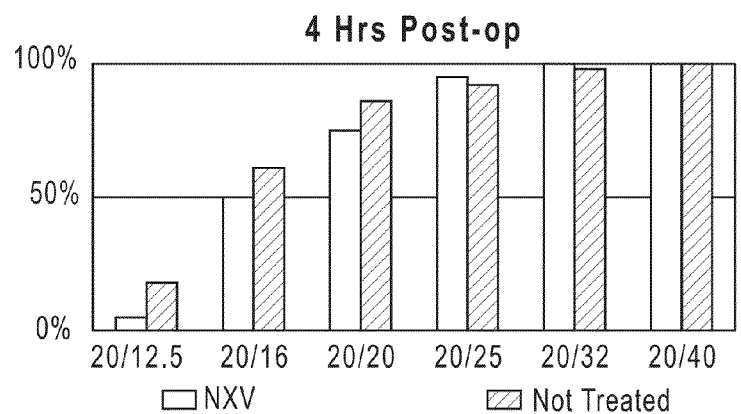
Figure 12F:
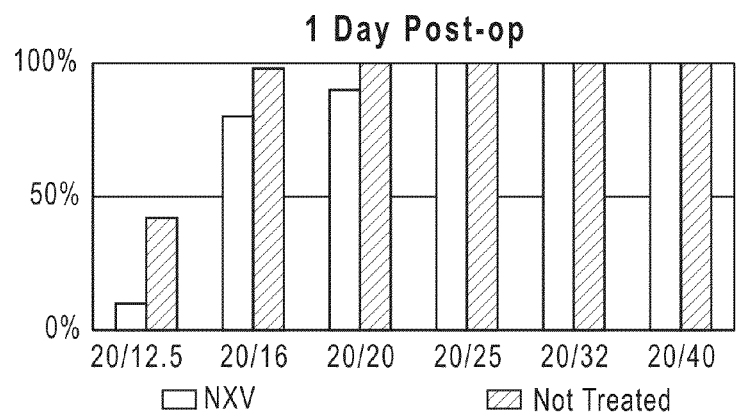

The ability of the covering to decrease the time of visual recovery compared to the time of visual recovery without the covering was confirmed by measuring the binocular visual acuity in a population of patients following LASIK. FIGS. 12A-12F show histograms representing the binocular visual acuities of a population of patients (n=20) with and without a covering provided by the present disclosure applied to an eye following LASIK. Each histogram represents the percent of the population of patients that reported the indicated binocular visual acuity or better. For example, as shown in FIG. 12A, immediately following LASIK, about 60% of patients wearing a covering provided by the present disclosure reported 20/20 vision, compared to only about 20% of patients not wearing a covering. Similar improvements in vision for the population of patients wearing a covering is observed at 30 minutes (FIG. 12B), 1 hour (FIG. 12C), 2 hours (FIG. 12D), 4 hours (FIG. 12E), and up to 1 day (FIG. 12F) following surgery. These results demonstrate that whether or not a covering is applied following LASIK, binocular visual acuity gradually improves during the recovery period. However, for those patients wearing a covering, binocular visual acuity is restored much more rapidly compared to LASIK patients not wearing a covering.

Figure 13:
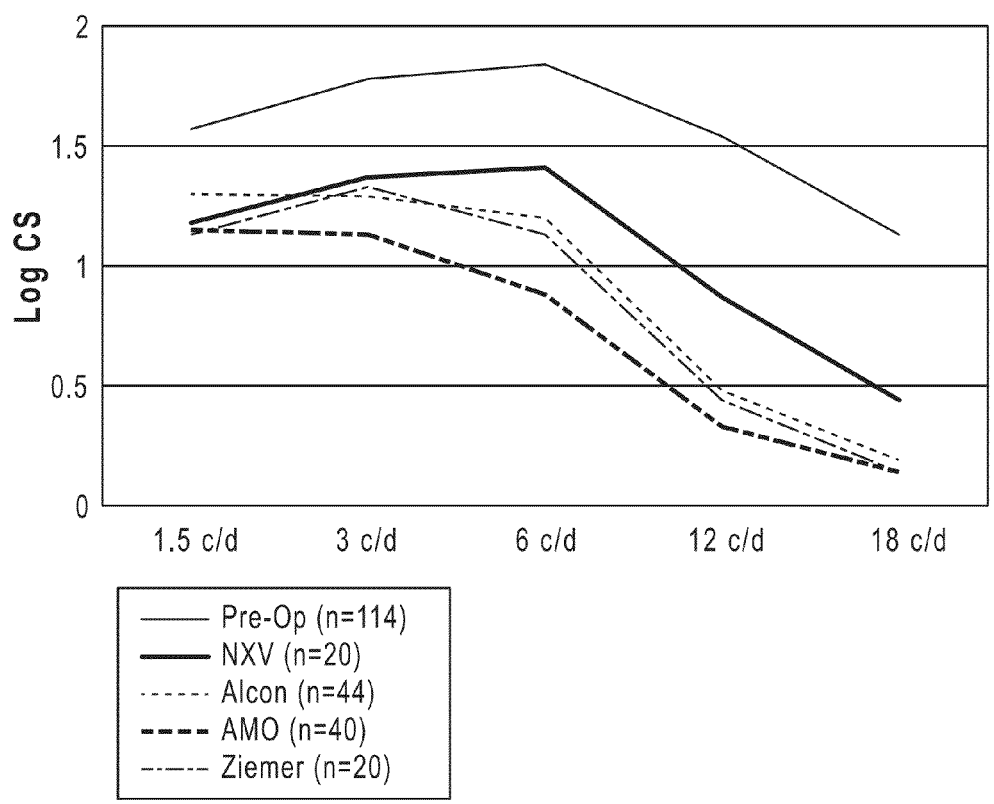
FIG. 13 is a graph of the frequency-dependent monocular mesopic contrast sensitivity for a population of patients prior to LASIK surgery (pre-op), following LASIK surgery with various surgical platforms (Alcon, AMO, and Ziemer) without wearing a covering following surgery, and following LASIK using the Alcon platform and with post-LASIK patients wearing a covering provided by the present disclosure following surgery (NXV).
Figure 14:
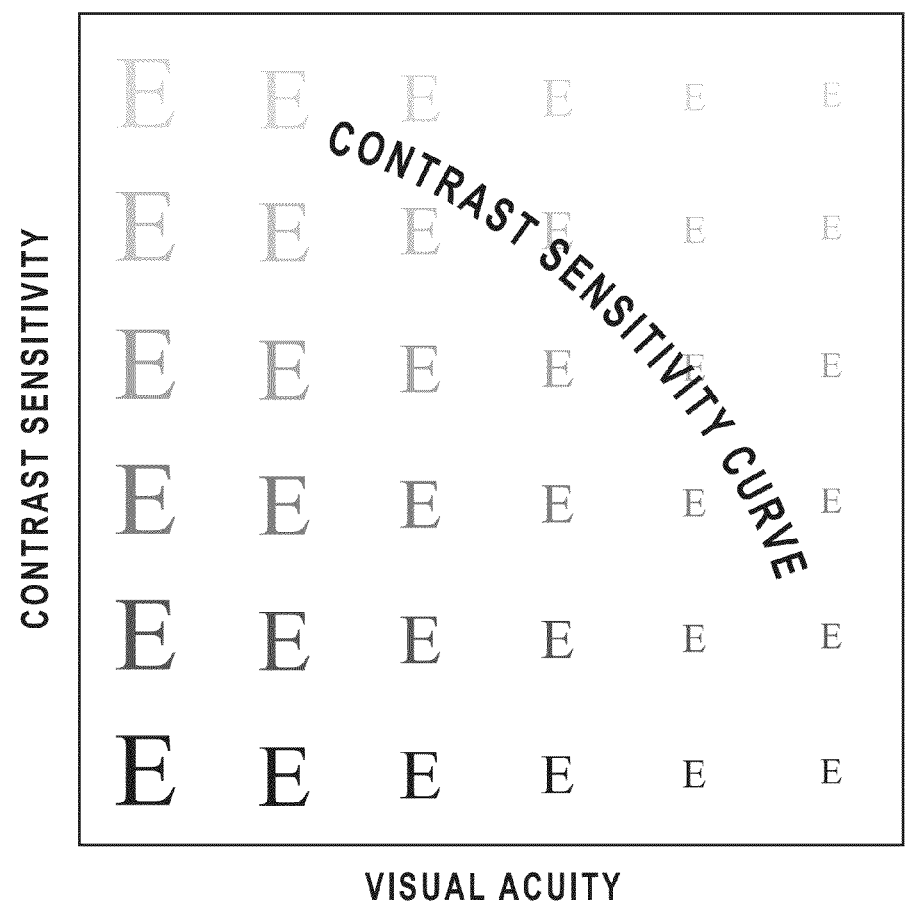
FIG. 14 shows the relationship between contrast sensitivity and visual acuity and also the typical contrast sensitivity for normal vision (contrast sensitivity curve).

Coverings provided by the present disclosure also improve contrast sensitivity following LASIK surgery. Contrast sensitivity is a measure of the ability to discern between luminances of different levels in a static image. Contrast sensitivity can depend, for example, on the spatial frequency of an image. The improvement in contrast sensitivity using a covering provided by the present disclosure is provided in FIG. 13. FIG. 13 shows the monocular mesopic contrast sensitivity (log CS) as a function of the spatial frequency. The uppermost curve presents the frequency-dependent contrast sensitivity of a population of patients prior to LASIK. Following LASIK surgery using the Alcon, AMO, or Ziemer LASIK platforms, the contrast sensitivity, and in particular the high frequency contrast sensitivity, is decreased. Post-surgical edema caused an even depression of contrast sensitivity at all spatial frequencies. The additional decreased high frequency contrast sensitivity (from 12 c/d to 18 c/d) is attributed to refractive error and/or higher order aberrations. As shown in FIG. 13, when a covering provided by the present disclosure is applied to an eye following LASIK surgery, the high spatial frequency contrast sensitivity is improved thereby indicating that a covering provides a sharper retinal image quality. These results further confirm that coverings provided by the present disclosure function to predominately correct refractive error and/or higher order optical aberrations rather than to enhance vision by affecting post-LASIK edema immediately following surgery. FIG. 14 shows the relationship between contrast sensitivity and visual acuity and the typical contrast sensitivity for normal vision (contrast sensitivity curve).

Figure 15:
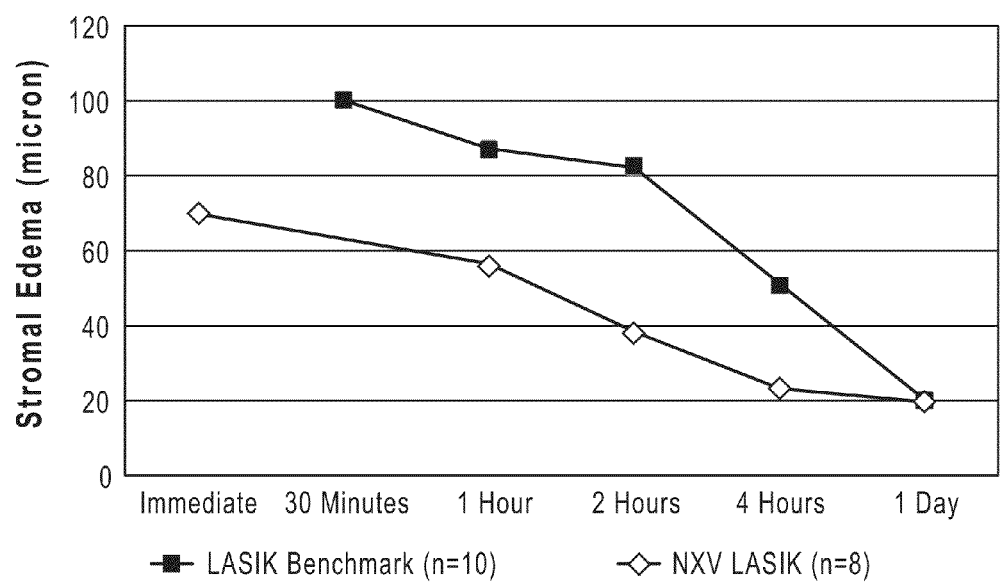
FIG. 15 is a graph showing the decrease in stromal edema in eyes of a population of patients following LASIK surgery without wearing a covering (LASIK benchmark) and wearing a covering provided by the present disclosure (NXV LASIK).

Nevertheless, coverings provided by the present disclosure also resolve edema over time resulting in reduced scattering and veiling glare and thereby restore vision faster. As shown in FIG. 15, post-operative edema was measured with and without the covering. Thirty-minutes following surgery, with the covering in place, edema caused by the LASIK procedure was reduced from about 100 μm to about 60 μm. The improvement in edema was observed throughout the 24-hour recovery period.

Coverings provided by the present disclosure also reduce post-LASIK discomfort as reflected in reduced overall discomfort, reduced outdoor photophobia, and reduced burning sensation. Following LASIK surgery, the majority, e.g., greater than 50%, of patients report light sensitivity (photophobia) and a burning sensation during the first 4 hours. In one study, wearing a covering provided by the present disclosure, 85% of patients (n=20 patients) reported no discomfort symptoms. Further details of studies measuring post-LASIK discomfort are summarized in FIG. 16A, FIG. 16B, FIG. 17A, FIG. 17B, FIG. 18A, and FIG. 18B.

Figure 16A:
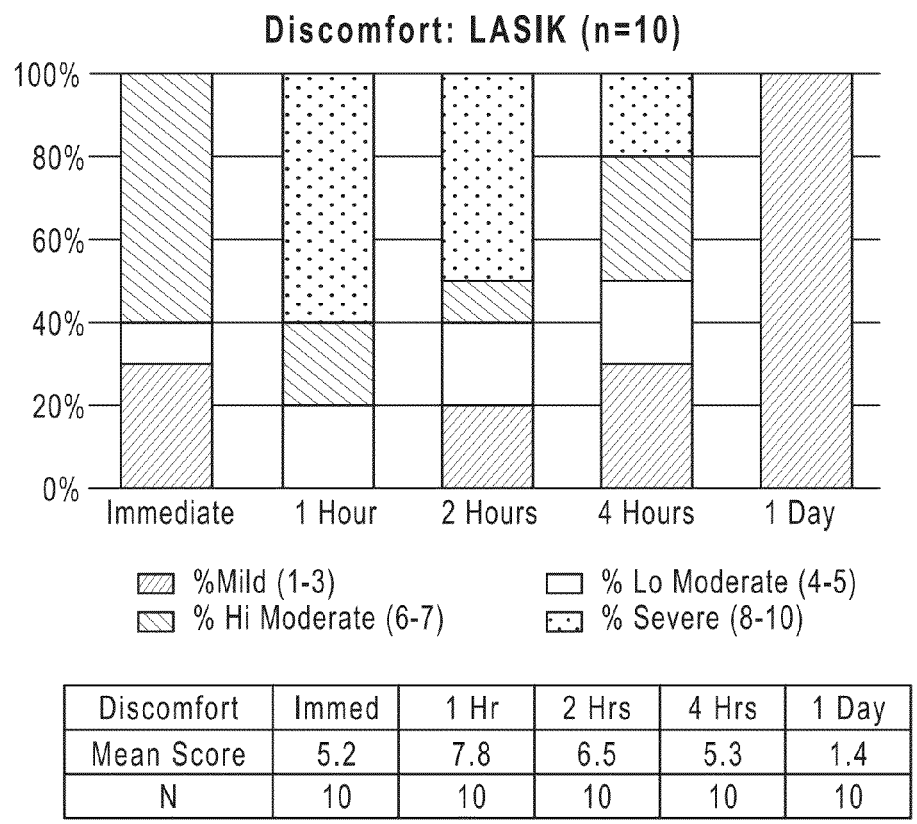
FIG. 16A shows (a) a histogram reflecting the percent of patients (n=10) experiencing various levels of overall discomfort with time following LASIK surgery; and (b) a table of the mean overall discomfort score based on the histogram, in a population of LASIK patients without the covering.
Figure 16B:
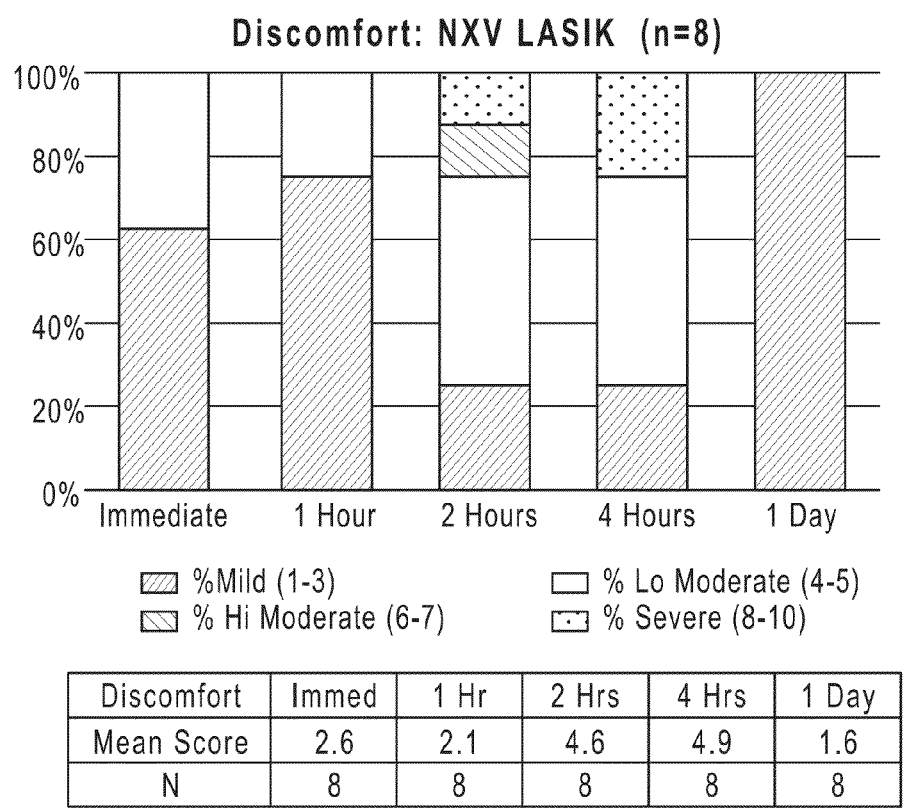
FIG. 16B shows (a) a histogram reflecting the percent of patients (n=8) experiencing various levels of overall discomfort with time following LASIK surgery; and (b) a table of the mean overall discomfort score based on the histogram, in a population of patients wearing a covering provided by the present disclosure.

Histograms summarizing the percent of patients reporting various degrees of overall discomfort following LASIK surgery are provided in FIG. 16A and FIG. 16B. As shown in FIG. 16A, without a covering, as reflected in the histograms, the mean overall discomfort score was 5.2 immediately following surgery, 7.8 one hour following surgery, and 6.5 two hours following surgery. In comparison, as shown in FIG. 16B, when a covering was worn, the mean overall discomfort score was 2.6 immediately following surgery, 2.1 one hour following surgery, and 4.6 two hours following surgery. The differences in the mean overall discomfort scores immediately following surgery, at one hour following surgery, and at two hours following surgery are statistically significant ($\alpha < 0.01$). Thus, application of a covering to an eye improves the overall discomfort during at least the first two hours following LASIK surgery.

Figure 17A:
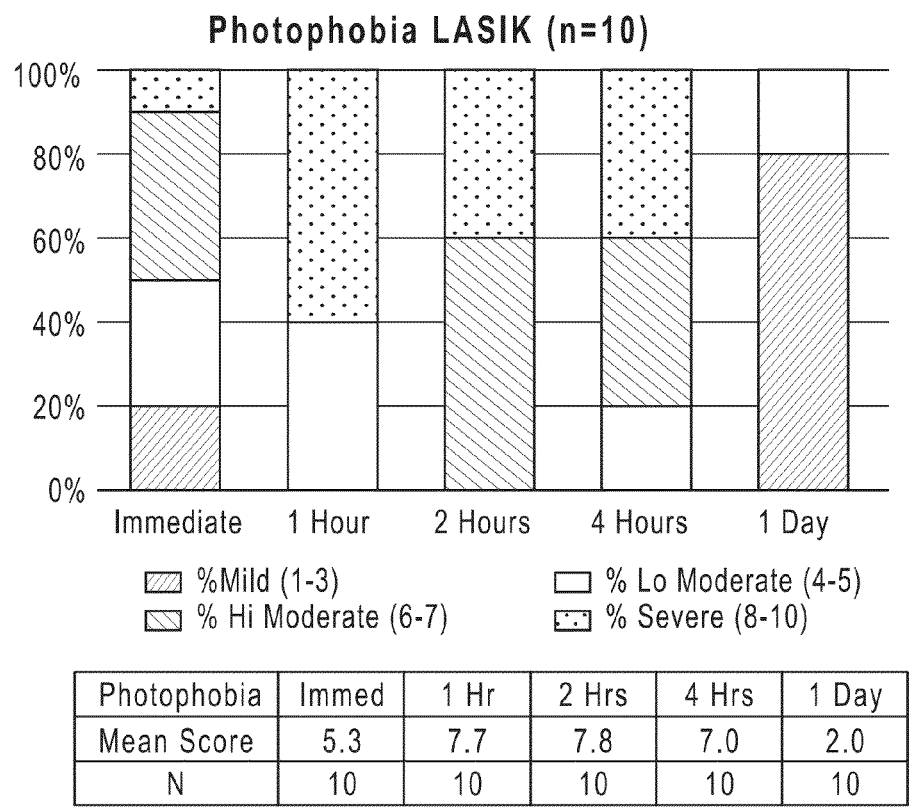
FIG. 17A shows (a) a histogram reflecting the percent of patients (n=10) experiencing various levels of outdoor photophobia with time following LASIK surgery; and (b) a table of the mean outdoor photophobia score based on the histogram, in a population of untreated patients.
Figure 17B:
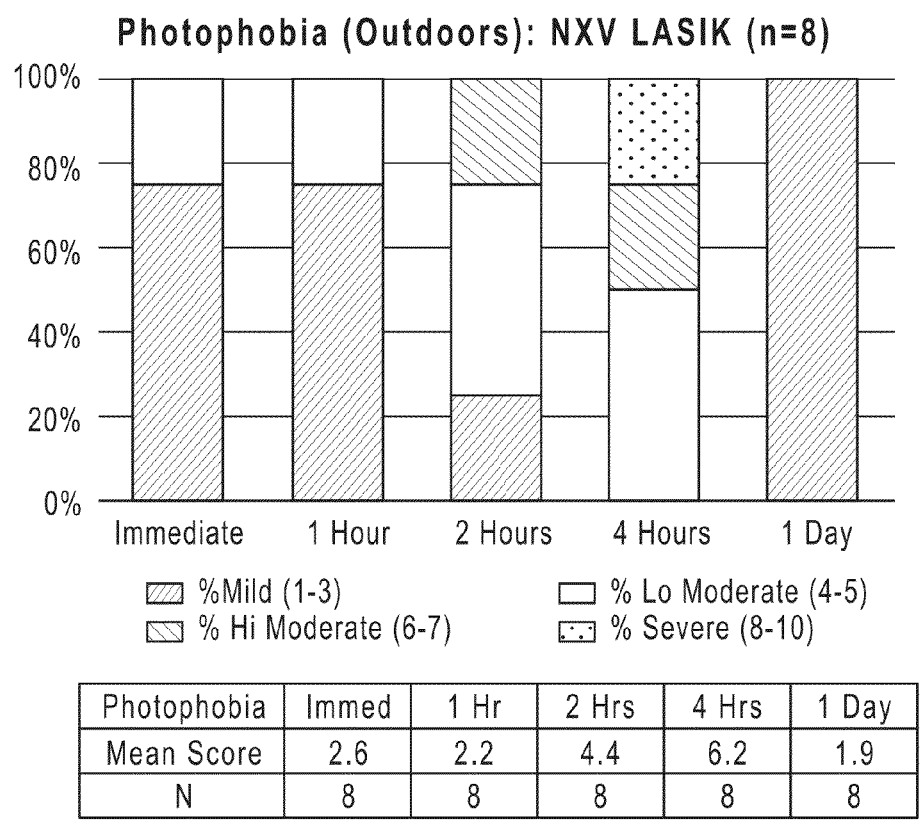
FIG. 17B shows (a) a histogram reflecting the percent of patients (n=8) experiencing various levels of outdoor photophobia with time following LASIK surgery; and (b) a table of the mean outdoor photophobia score based on the histogram, in a population of patients wearing a covering provided by the present disclosure.

Similar improvements are observed for outdoor photophobia. FIG. 17A and FIG. 17B show histograms of outdoor photophobia following LASIK surgery. For patients not wearing a covering, the mean outdoor photophobia was 5.3 immediately following LASIK surgery, 7.7 one hour following surgery, and 7.8 two hours following surgery. As shown in FIG. 17B, when a covering is applied to the eye following LASIK surgery, the corresponding mean outdoor photophobia scores are 2.6 immediately following surgery, 2.2 one hour following surgery, and 4.4 two hours following surgery. The differences in the mean outdoor photophobia scores immediately following surgery, at one hour following surgery, and at two hours following surgery are statistically significant ($\alpha < 0.01$). Thus, the results presented in FIG. 17A and FIG. 17B demonstrate that application of a covering to an eye improves the outdoor photophobia during at least the first two hours following LASIK surgery.

Figure 18A:
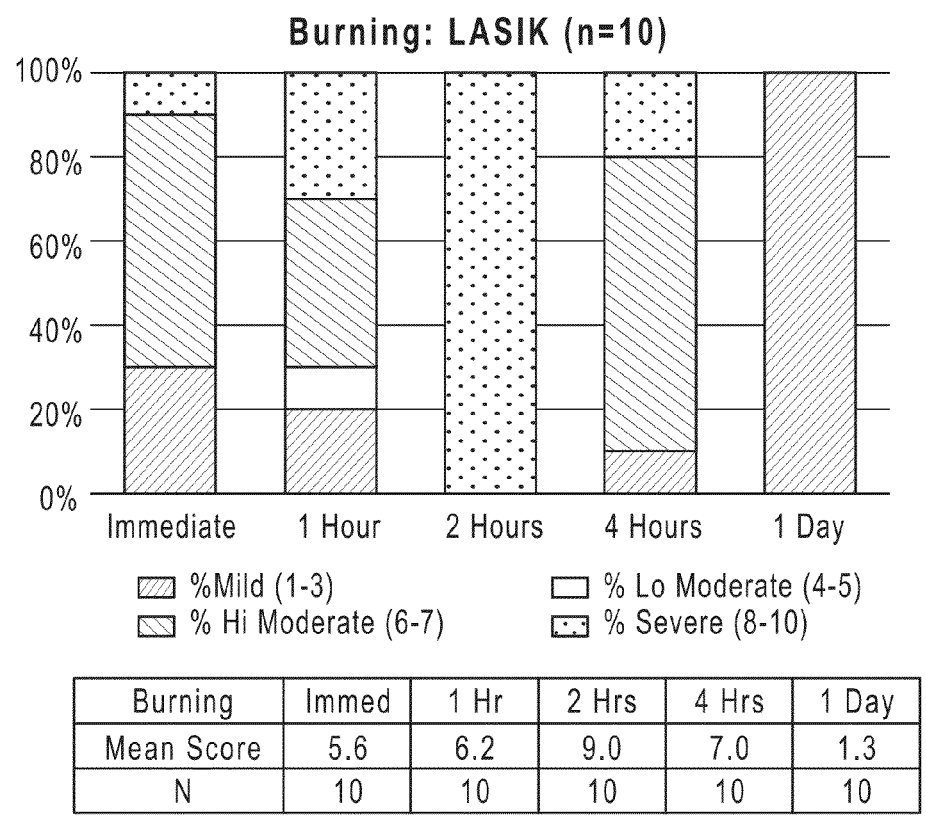
FIG. 18A shows (a) a histogram reflecting the percent of patients (n=10) experiencing various levels of burning sensation with time following LASIK surgery; and (b) a table of the mean burning sensation score based on the histogram, in a population of untreated patients.
Figure 18B:
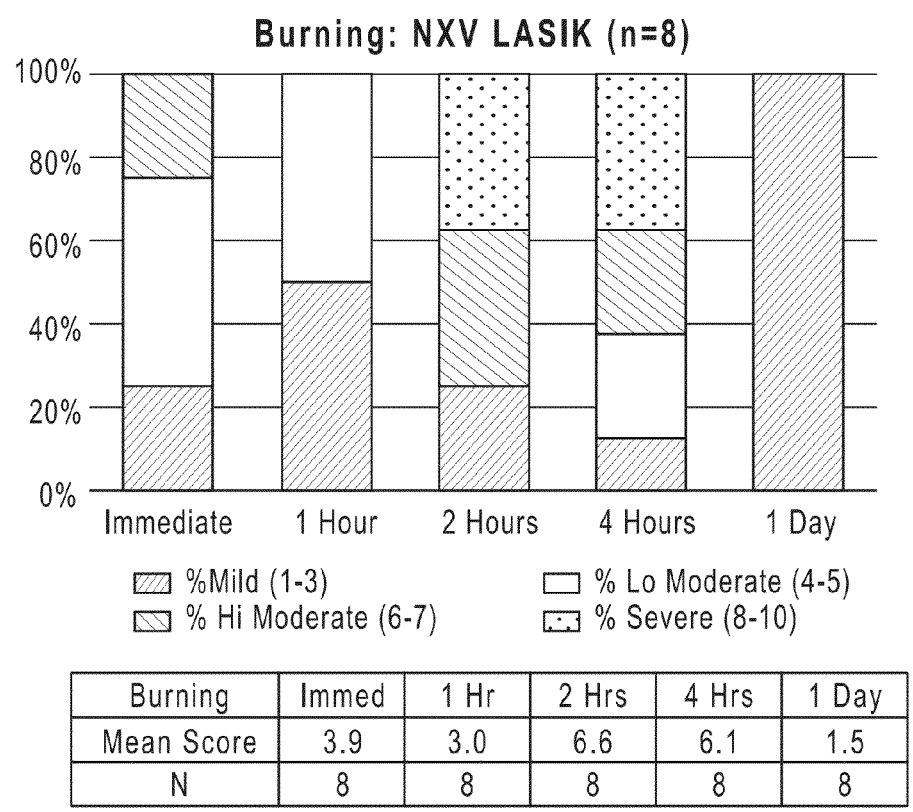
FIG. 18B shows (a) a histogram reflecting the percent of patients (n=8) experiencing various levels of burning sensation with time following LASIK surgery; and (b) a table of the mean burning sensation score based on the histogram, in a population of patients wearing a covering provided by the present disclosure.

Coverings can also reduce the burning sensation during the first few hours following LASIK. As shown in FIG. 18A, for patients not wearing a covering, the mean burning sensation score was determined to be 5.6 immediately following surgery, 6.2 one hour following surgery, and 9.0 two hours following surgery. In comparison, as shown in FIG. 18B, when a covering is applied to the eye immediately following LASIK surgery, the mean burning sensation score was determined to be 3.9 immediately following surgery, 3.0 one hour following surgery, and 6.6 two hours following surgery. The differences in the mean burning sensation scores one hour following surgery and two hours following surgery are statistically significant ($\alpha < 0.01$). Thus, coverings provided by the present disclosure significantly improve discomfort associated with a burning sensation at least within the first two hours following LASIK surgery.

Figure 19:
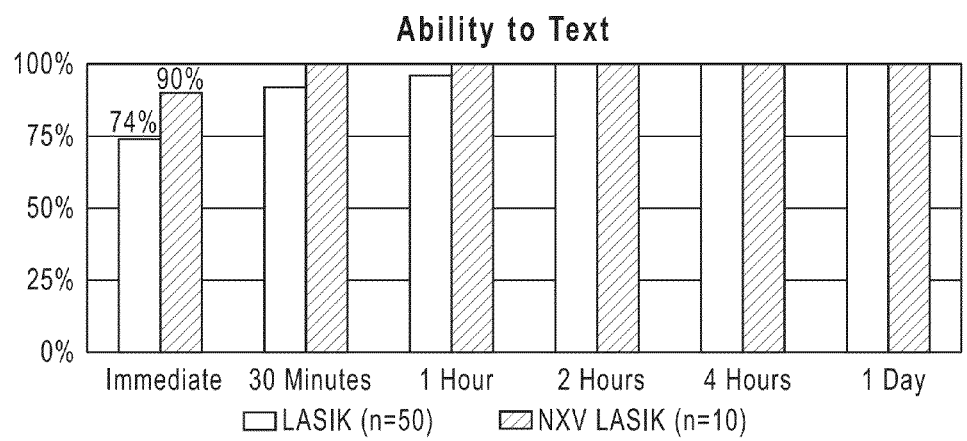
FIG. 19 shows a histogram of the percent of patients able to text at various times following LASIK surgery without treatment (LASIK) and with treatment according to methods provided by the present disclosure (NXV LASIK).

The ability of coverings to improve functional measures of visual recovery following LASIK surgery was also assessed. FIG. 19 shows the ability of a patient to text using a mobile telecommunications device such as a mobile phone at various times following LASIK surgery. To assess texting ability, patients were encouraged to text and to report their ability to text at each time interval. As is shown in FIG. 19, immediately following LASIK surgery, most patients were comfortable texting, however, measurably more patients wearing a covering were texting immediately following surgery, at 30 minutes following surgery, and at one hour following surgery, compared to those patients not wearing a covering.

Figure 20:
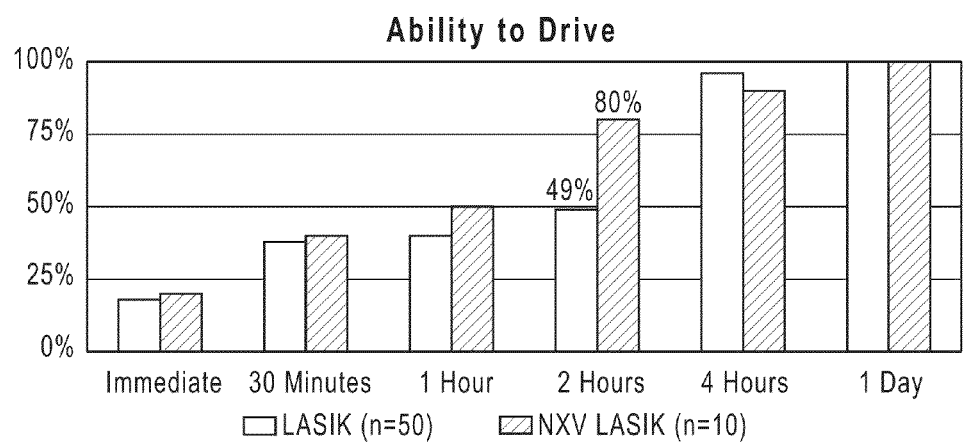
FIG. 20 shows a histogram of the percent of patients who feel comfortable driving at various times following LASIK surgery without treatment (LASIK) and with treatment according to methods provided by the present disclosure (NXV LASIK).

A similar improvement in the rate of recovery in a patient's perceived ability to drive following LASIK surgery when wearing a covering was also observed. FIG. 20 shows the percent of patients who felt comfortable driving at various times following LASIK surgery. Overall, patients who were wearing a covering felt more comfortable driving during the first 4 hours following LASIK surgery than did patients who did not wear a covering.

Fitting a covering to a patient's eye involves, at least in part, selecting a covering that at least partially restores vision following LASIK surgery, increases the rate at which optimal visual acuity is achieved, and improves patient comfort. In general, the parameters associated with the central 3 mm region of a covering determine properties associated with vision. In general, the parameters associated with the mid-peripheral 5 mm region, e.g., the intermediate portion, of a covering correlates with patient comfort. Furthermore, in generally there is little or no interaction between the fit of the 3 mm and the 5 mm regions. In certain embodiments, recommended fitting ranges for the 3 mm central region is from −1.0D to −2.5D than the corresponding central region of the cornea; and for the 5 mm mid-peripheral region is from about −1.0D to about −2.5D than the corresponding region of the cornea. In certain embodiments, recommended fitting ranges for the 3 mm central region is from −2.0D to −3.0D than the corresponding central region of the cornea; and for the 5 mm mid-peripheral region is from about −0.0D to about −1.5D than the corresponding region of the cornea.

Because a range of covering curvatures can be fit to a range of corneal curvatures in treating post-LASIK vision, relatively few covering choices need be manufactured thereby reducing costs associated with stocking and facilitating the fitting procedure.

The fitting strategy for selecting a covering shape for a patients eye involves, at least in part, determining the curvature of the cornea of the eye of the patient, and selecting a covering that has a center curvature that is less than, e.g., flatter than, the curvature of the cornea. In certain embodiments, the curvature of the selected covering is from −1.0D to −2.0D than the curvature of the cornea, from −1.0D to −2.5D than the curvature of the cornea, from −1.0 D to −3.0 D than the curvature of the cornea, and in certain embodiments, from 0D to −3.0D than the curvature of the cornea. In certain embodiments, the curvature of the selected covering is from −1.5D to −2.5D than the curvature of the cornea, from −1.5D to −3.0D than the curvature of the cornea, and in certain embodiments, from −1.5D to −3.5D than the curvature of the cornea.

Figure 21:
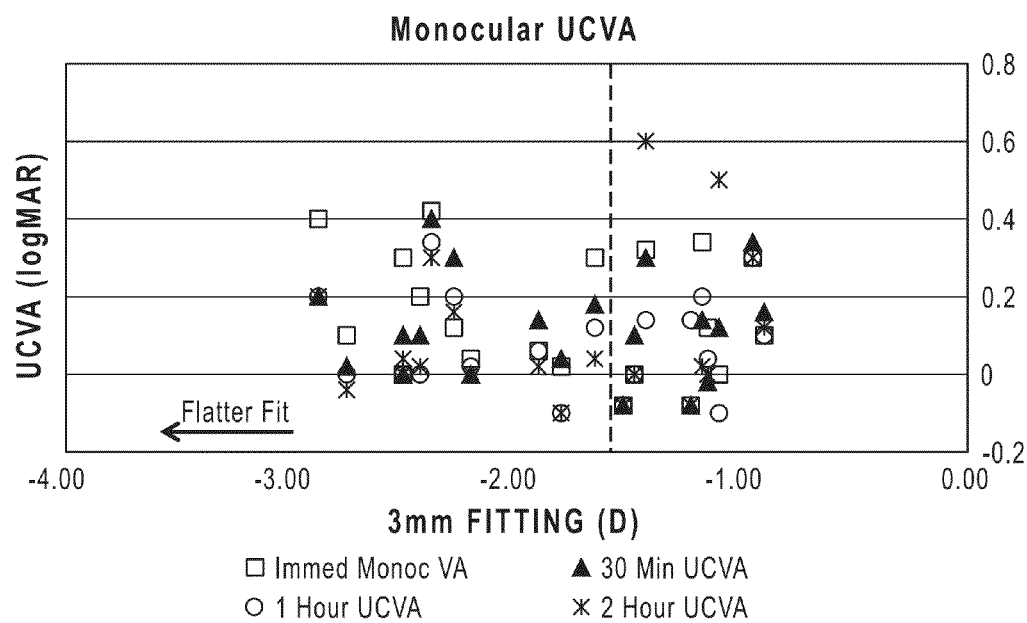
FIG. 21 is a scatter chart showing the monocular UCVA at various times following LASIK surgery for patients wearing coverings having central (3 mm) curvatures between about −1.0D and −3.0D compared to the central curvature of the cornea.

The visual acuity following LASIK surgery was measured for patients wearing coverings having different curvatures and at various times following surgery. The data is summarized in FIG. 21. The data indicates that coverings having a flatter central fit, such as from −1.5D to about −3.0D than the curvature of the cornea improve monocular UCVA, particularly at 2 hours following LASIK surgery. The region of the central fit is defined as the central 3 mm diameter center of the covering and the corresponding 3 mm diameter center of the cornea to which the covering is applied.

Figure 22:
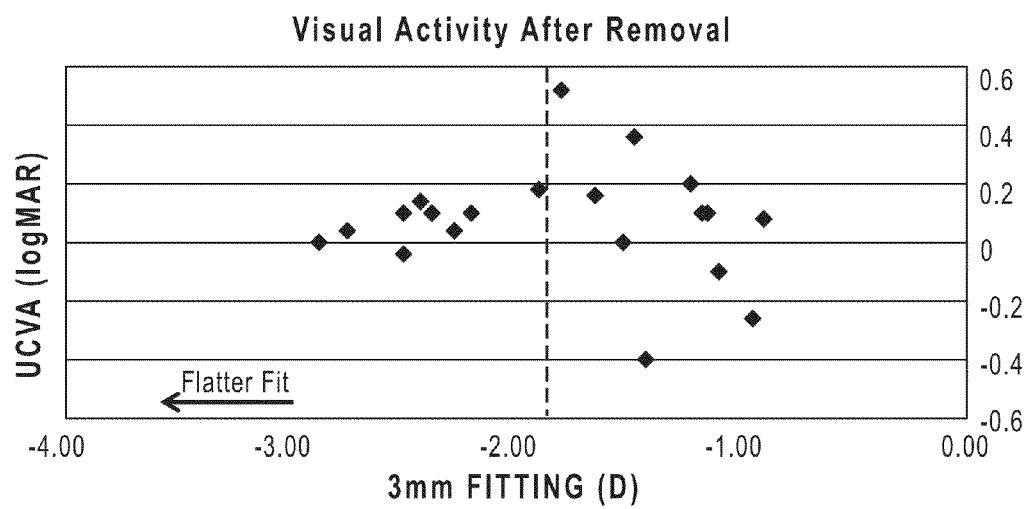
FIG. 22 is a scatter chart showing the decrease in visual acuity (UCVA) after coverings having different central (3 mm) curvatures are removed from a patient's eye.

A flatter central fit also provides improved vision by avoiding a decrease in vision when the covering is removed from the cornea. In general, when a covering provided by the present disclosure is removed from the cornea, a patient experiences a temporary decrease in vision that lasts from 0 minutes to 180 minutes. This decrease in vision occurs, whether the covering is removed within the first 2 hours, at 2 hours, or up to 24 hours after the covering has been applied to a patient's eye. As shown in FIG. 22, coverings that have a curvature that is from about −2.0D to about −3.0D the curvature of the cornea exhibit less of a reduction in the UCVA when removed from the patient's eye compared to coverings having a steeper profile.

Figure 23:
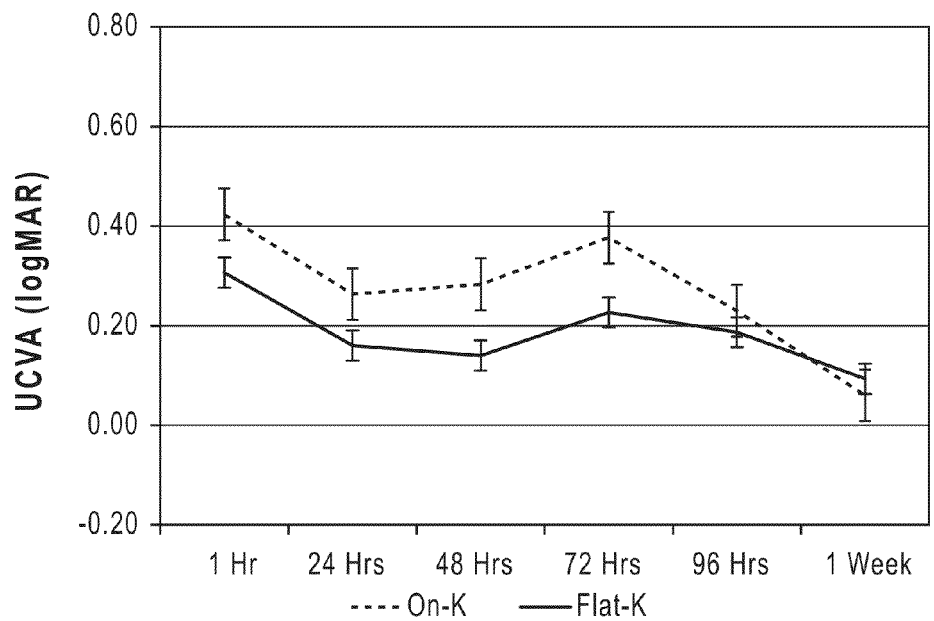
FIG. 23 is a graph showing the UCVA following photorefractive keratectomy (PRK) surgery in a population of patients (n=6) wearing a covering having a central curvature about the same as the central curvature of the cornea (on-K), and a population of patients wearing a covering having a central curvature from about 1.0D to about 2.5D flatter than the curvature of the cornea (flat-K), e.g., having a curvature −1.0D to about −2.5D that of the cornea.
Figure 24:
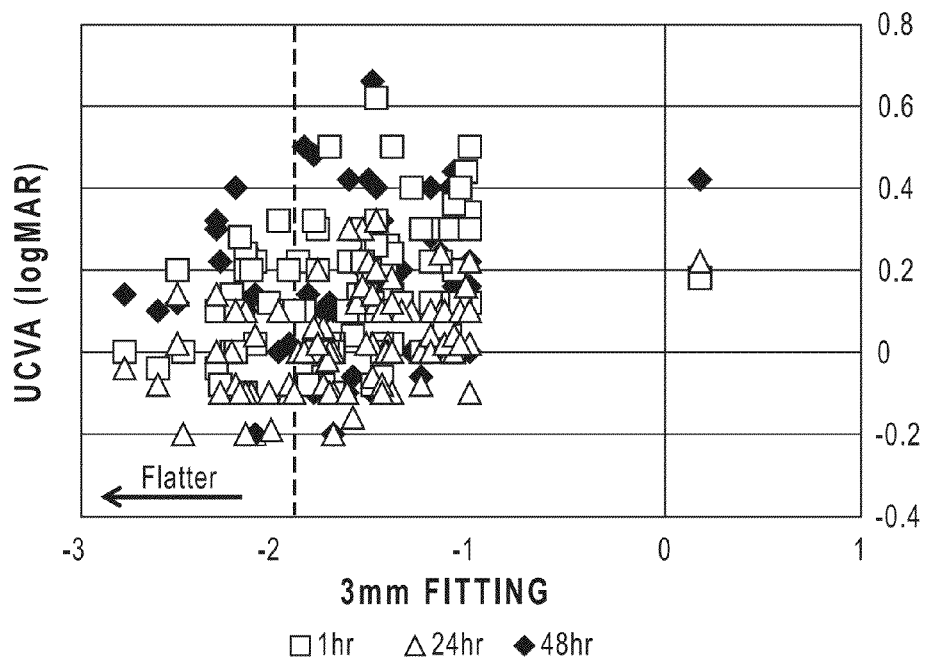
FIG. 24 is a scatter chart showing the UCVA at various times following LASIK surgery for a population of patients (Durrie n=89) wearing coverings having a curvature about −1.0D to about −3.0D flatter than the curvature of the post-PRK cornea.

In addition to providing enhanced visual acuity, coverings having a flatter central fit can enhance the predictability of post-operative UCVA within a population of patients. As shown in FIG. 23, the UCVA of patients was determined at various times following PRK surgery. One group of patients wore coverings having a curvature equivalent to the corneal curvature (on-K), and a second group of patients wore coverings having a profile that was −1.0D to −2.5D the curvature (flat-K) of the cornea. In the group of patients wearing coverings having a steeper profile (on-K) the variation in the visual acuity among the patients as reflected by the error bars associated with the measured UCVA was greater than the variation in the visual acuity among the patients wearing coverings having a flatter curvature (flat-K). This difference was apparent at all times through 1 week following PRK surgery. Similar data is presented as a scatter plot in FIG. 24 for a study including 89 patients in which individual patients wore coverings having different profiles. A similar enhanced predictability of UCVA among patients following LASIK surgery can be expected.

It is believed that coverings having a steeper 5 mm mid-peripheral profile (curvature at 5 mm from the center of the covering) e.g., steeper than −1.0D, are more susceptible to trapping air bubbles during placement on the cornea, and that coverings having a flatter 5 mm fit, e.g., flatter than −2.5D, may slow epithelial healing. However, it has also been determined that coverings having a flatter 5 mm mid-peripheral fit, e.g., from −0.01D to −1.5D result in improved comfort at 2 days following LASIK surgery. Issues concerning potential bubble entrapment may be addressed using the inverted placement technique for placing a covering on a patient's eye.

Figure 25:
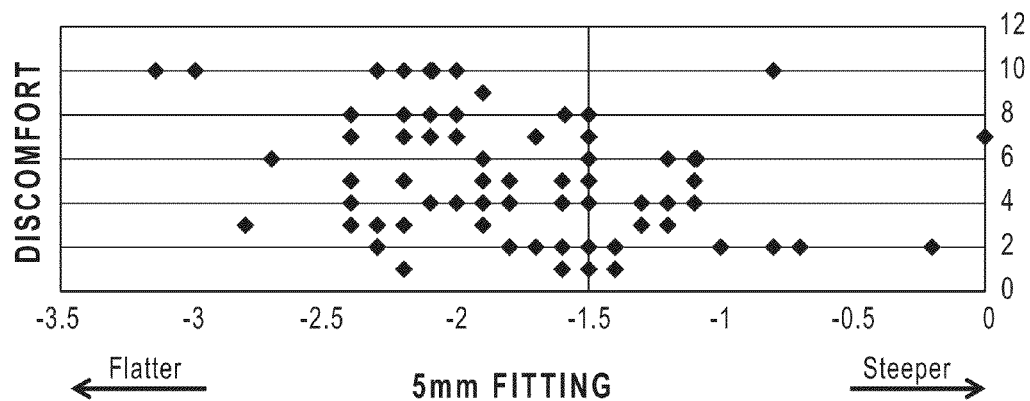
FIG. 25 is a scatter chart showing the discomfort two days (48 hours) following PRK surgery in a population of patients (Durrie n=89) wearing coverings having different mid-periphery (5 mm) curvatures.

The ability of coverings having a flatter 5 mm fit to improve post-operative comfort is presented in FIG. 25, which shows a general trend toward improved 48-hour post-PRK comfort with coverings having a flatter 5 mm mid-peripheral fit, such as for coverings that are 1.5D to 3.0D flatter than the cornea, e.g., −1.5D to −3.0D coverings. A similar correlation between mid-periphery fit and comfort is expected for coverings provided by the present disclosure used following LASIK.

Figure 26:
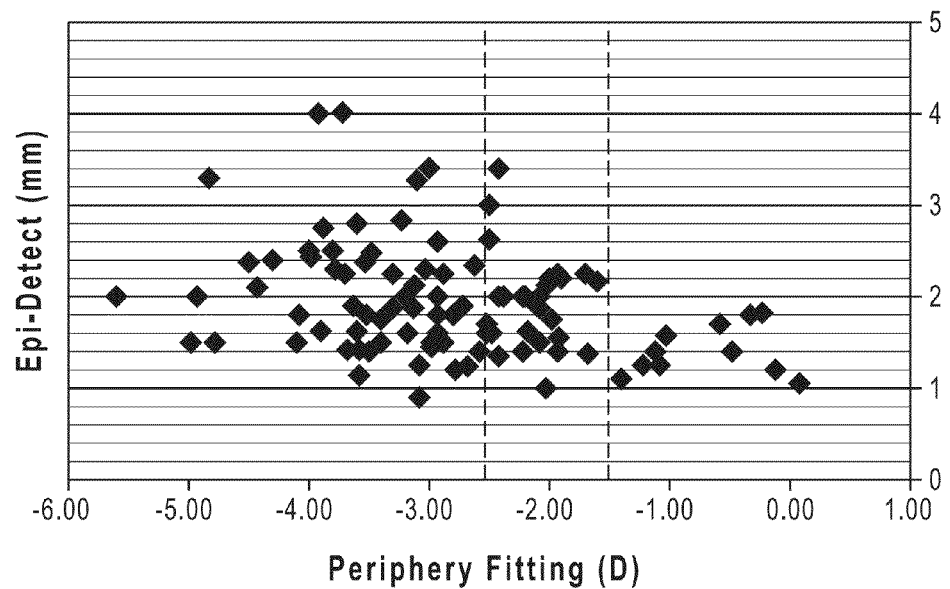
FIG. 26 is a scatter chart showing the area of epithelial defects two days (48 hours) following PRK surgery in patients (Durrie n=89) wearing coverings having different mid-periphery (5 mm) curvatures from about 0D to about −6D.
Figure 27:
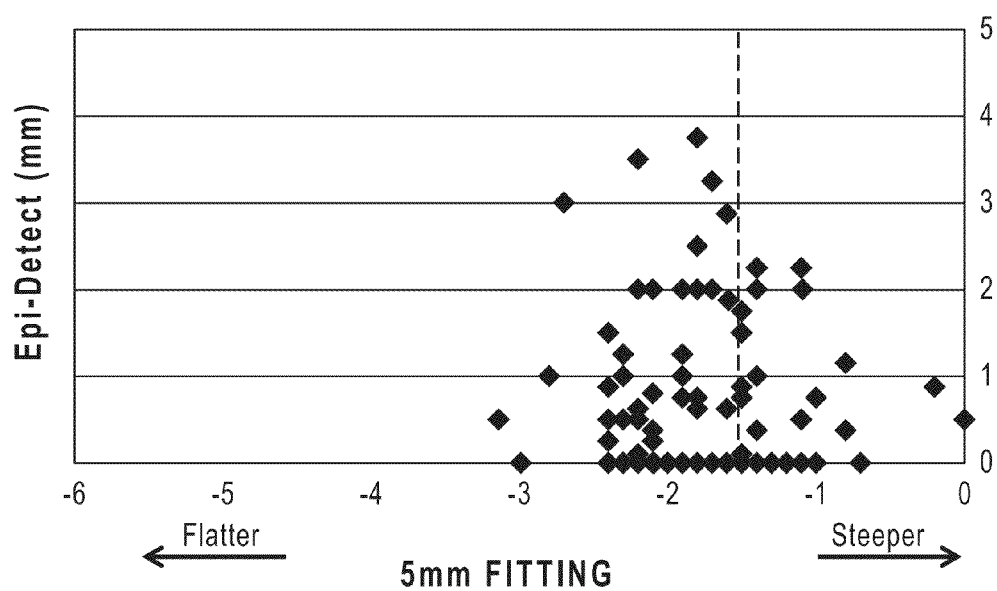
FIG. 27 is a scatter chart showing the area of epithelial defects two days (48 hours) following PRK surgery in patients (Durrie n=89) wearing coverings having different mid-periphery (5 mm) curvatures from about 0D to about −3D.

Factors associated with selecting an appropriate mid-periphery 5 mm fit include selecting a mid-peripheral curvature and/or shape to optimize epithelial healing and to minimize the entrapment of air bubbles during placement. The number of epithelial defects was measured after coverings having different mid-peripheral curvatures were applied to eyes following PRK surgery. As shown in FIG. 26, the number of post-PRK epithelial defects decreased for more steeply curved coverings. FIG. 27 shows the number of post-PRK epithelial defects for coverings having from about 0 to about −3.0 peripheral curvature, and indicates that a mid-peripheral curvature of less than −1.5D can provide improved performance by enhancing epithelial healing and by minimizing the entrapment of air bubbles. Although LASIK does not involve the extent of epithelial damage as in PRK; nevertheless, in LASIK the epithelium is transected to permit ablation of the stroma. When the corneal flap is replaced over the ablated cornea, the transected epithelium must heal. In fact one of the complications of LASIK is epithelial ingrowth in which epithelial cells begin to grow underneath the corneal flap. It is estimated that about 30% of LASIK retreatment procedures have epithelial ingrowth issues. Therefore, appropriate selection of the mid-periphery 5 mm fit is expected to benefit epithelial recovery in LASIK patients, as was demonstrated for PRK patients.

Coverings provided by the present disclosure can also reduce the risk of diffuse lamellar keratitis (DLK). DLK is a nonspecific sterile inflammatory response that can result from refractive surgeries such as LASIK. Symptoms range from mild photophobia and/or mild decreased vision to severe decreased vision. Intraoperative epithelial defects are considered to be one of the causes of DLK. The ability of a covering to facilitate the ability of the LASIK flap to adhere to the ablated cornea and restore the epithelium following surgery can reduce DLK caused by epithelial defects and others.

In summary, coverings provided by the present disclosure at least provide improved vision following LASIK surgery, increase post-operative comfort, and increase the rate of functional visual recovery. These improvements are particularly apparent during the first two hours following LASIK surgery.

A covering may be removed at any appropriate time after being applied to a patient's eye, which may at least in part be determined by the judgment of the physician and/or the convenience of the patient. For example, a covering may be removed 2 hours, 4 hours, 8 hours, 12 hours, 24 hours, or any other time following application. In certain embodiments, a covering is removed about 4 hours following LASIK surgery. It has been observed that when a covering is removed from an eye within a few hours following application and during the recovery period, such as about 2 hours following surgery and application, patient comfort may be compromised. For example, when a covering is removed about 2 hours following surgery and application, a patient may experience photophobia and a burning sensation similar to that of a LASIK patient without a covering. Nevertheless, this discomfort is temporary, and is less severe than is experienced by a patient without the covering applied to the eye. Therefore, in certain methods, a covering may be applied to an eye immediately following LASIK surgery and removed within the first two hours and still achieve benefits of enhanced vision and improved comfort.

A covering may be removed from the eye by the physician, by other medical personnel, or by the patient. In general, it is desirable that a covering be removed by grasping the outer periphery of the covering and pulling the covering from the eye.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of treating an eye of a patient following LASIK refractive surgery, the eye comprising a cornea having an anterior surface, an ablated stroma, and a flap having an anterior surface, the flap surrounded by epithelium and a sclera, the ablated stroma providing the anterior surface of the flap a post-ablation profile when the flap is disposed on the ablated stroma, the method comprising:
   providing a covering comprising:
      an inner portion characterized by an inner rigidity, and comprising an upper surface, a lower surface, and a material characterized by an inner modulus from 10 MPa to 70 MPa; and
      an outer portion characterized by an outer rigidity, and comprising an upper surface, a lower surface, and a material characterized by an outer modulus;
   applying the covering against the eye so that the covering flexes with the lower surface of the inner portion disposed along the anterior surface of the flap and partially conforming to the post-ablation profile of the anterior surface; and
   resisting movement of the inner portion relative to the flap by engaging the lower surface of the outer portion with the eye along the epithelium, the sclera, or a combination thereof.

2. The method of claim 1, wherein:
   the lower surface of the inner portion is characterized by at least one inner radius of curvature; and
   the outer portion comprises a peripheral portion having a lower peripheral surface characterized by at least one peripheral radius of curvature; and
   further comprising engaging a peripheral edge of the flap and the adjacent epithelium with the lower peripheral surface of the covering so that the eye views through the flap and the inner portion.

3. The method of claim 2,
   wherein the at least one inner radius of curvature comprises a radius of curvature that corresponds to or is less than that associated with the optical power of the ablated stroma; and
   further comprising deforming the inner portion during the applying of the covering so that the upper surface of the inner portion optically conforms to the anterior surface of the flap.

4. The method of claim 1,
wherein the outer portion comprises a peripheral portion and one or more intermediate portions, each of the one or more intermediate portions is independently characterized by an intermediate radius of curvature; and
further comprising inhibiting movement of the inner portion relative to the eye by deforming at least the peripheral portion during the applying of the covering so as to promote motion-inhibiting engagement of the peripheral portion against the epithelium, the sclera, or a combination thereof, of the eye.

5. The method of claim 1, wherein the inner portion is characterized by a substantially uniform thickness.

6. The method of claim 1, wherein the inner portion is characterized by a shape that does not substantially correct vision.

7. The method of claim 1, wherein the inner rigidity is from $1.2E^{-6}$ Pa-m$^3$ to $3.1E^{-3}$ Pa-m$^3$ and the outer rigidity is from $5.4E^{-9}$ Pa-m$^3$ to $1.5E^{-4}$ Pa-m$^3$.

8. The method of claim 1, wherein the inner portion is characterized by an index of refraction that corresponds substantially to the index of refraction of the cornea.

9. The method of claim 1, wherein the inner portion and the outer portion comprise a material selected from silicone, a silicone hydrogel, or a combination thereof.

10. The method of claim 1, wherein the inner modulus is greater than the outer modulus.

11. The method of claim 1, wherein the inner modulus is substantially the same as the outer modulus.

12. The method of claim 1, wherein:
the inner portion is configured to at least partially conform to the post-ablation profile of the flap;
the outer portion comprises at least one intermediate portion configured to at least partially conform to the anterior surface of the cornea; and
the outer portion comprises at least one peripheral portion configured to engage the epithelium, the sclera, or a combination thereof,
when the covering is applied to the eye.

13. The method of claim 12, wherein:
a lower surface of the inner portion is characterized by at least one inner radius of curvature from 6 mm to 11 mm;
a lower surface of the at least one intermediate portion is characterized by an intermediate radius of curvature from 7 mm to 9 mm; and
a lower surface of the peripheral portion is characterized by a peripheral radius of curvature from 8 mm to 15 mm.

14. The method of claim 1, wherein:
the lower surface of the inner portion is characterized by an inner radius of curvature that corresponds to or is less than that associated with the optical power of the cornea following refractive surgery; and
the inner portion is configured to deform during the application of the covering to the eye so that the upper surface of the inner portion optically conforms to the anterior surface of the flap.

15. A method of treating an eye of a patient following LASIK, the eye comprising a cornea comprising an anterior surface, an ablated stroma, an epithelium, and a sclera, the ablated stroma characterized by a post-ablation profile, the method comprising:
providing a covering comprising:
an inner portion comprising a first lower surface characterized by at least one inner radius of curvature and a material characterized by an inner modulus from 10 MPa to 70 MPa, wherein the at least one inner radius of curvature comprises a radius of curvature less than a radius of curvature of the post-ablation profile of the anterior surface of the cornea, wherein the inner portion is characterized by a substantially uniform thickness; and
an outer portion comprising a second lower surface characterized by at least one outer radius of curvature; and
applying the covering against the eye so that the covering flexes, with the inner portion at least partially disposed along and deforming so that an upper surface of the inner portion opposite the first lower surface of the inner portion optically conforms to the anterior surface of the cornea and at least a part of the outer portion engages the eye along the epithelium, the sclera, or a combination thereof.

16. The method of claim 1, wherein the inner rigidity is greater than the outer rigidity.

17. The method of claim 1, wherein the inner portion is characterized by a water content less than 10%.

18. The method of claim 15, wherein the inner portion is characterized by a water content less than 10%.

* * * * *